United States Patent [19]

Blalock et al.

[11] Patent Number: 5,077,195

[45] Date of Patent: * Dec. 31, 1991

[54] POLYPEPTIDES COMPLEMENTARY TO PEPTIDES OR PROTEINS HAVING AN AMINO ACID SEQUENCE OR NUCLEOTIDE CODING SEQUENCE AT LEAST PARTIALLY KNOWN AND METHODS OF DESIGN THEREFOR

[75] Inventors: J. Edwin Blalock; Kenneth L. Bost, both of Birmingham, Ala.; Eric M. Smith, Galveston, Tex.

[73] Assignee: Board of Reagents, The University of Texas System, Austin, Tex.

[*] Notice: The portion of the term of this patent subsequent to Sep. 5, 2006 has been disclaimed.

[21] Appl. No.: 829,709

[22] Filed: Feb. 19, 1986

Related U.S. Application Data

[63] Continuation-in-part of Ser. No. 708,001, Mar. 1, 1985.

[51] Int. Cl.$^5$ ............................................. C12Q 1/68
[52] U.S. Cl. .................................... 435/6; 435/172.3; 435/802; 436/501
[58] Field of Search .................... 436/501; 935/77, 78; 435/6, 803, 172.3, 68

[56] References Cited

FOREIGN PATENT DOCUMENTS

83/04053 11/1983 PCT Int'l Appl. .

OTHER PUBLICATIONS

Knutson, V. P., J. Biol. Chem. 263: 14146–14151 (1988).
European Search Report, 4 Aug., 1989.
Chem. Abstr., vol. 95, No. 19, Nov. 1981, p. 277; Abstract #164163t, Columbus, Ohio, US; J. Biro: "Comparative anal. of specif. in protein-protein interactions. Part II. The complementary coding of some proteins as the possible source of specificity in protein-protein interactions", Med. Hypotheses 1981, 7 (8), 981–983.
Chem. Abstr. vol. 94, No. 21, 5/21/81: p. 102, #16822f, Columbus, OH, US: Schreiber et al.; "Anti-alprenolol anti-idiotypic antibodies bind to beta-adrenergic receptors and modulate catecholamine-sensitive adenylate cyclase", & Proc. Natl. Acad. Sci. 1980, 77(12), 7385–9.
Mekler, Biofizika, VIV (4), 581–584.
Idlism Mendeleev Chem. J., 25:431–434 1980.
Biro, *Medical Hypotheses*, 7: 969–979, 981–993, 995–1007 (1981).

(List continued on next page.)

*Primary Examiner*—Amelia B. Yarbrough
*Attorney, Agent, or Firm*—Arnold, White & Durkee

[57] ABSTRACT

A method for determining the amino acid sequence of a polypeptide complementary to at least a portion of an original peptide or protein. In one aspect the method involves: (a) determining a first nucleotide sequence of a first nucleic acid coding for the biosynthesis of at least a portion of the original peptide or protein; (b) ascertaining a second nucleotide sequence of a second nucleic acid which base-pairs with the first nucleotide sequence of the first nucleic acid, the first and second nucleic acids pairing in antiparallel directions; and (c) determining the amino acid sequence of the complementary polypeptide by the second nucleotide sequence when read in the same reading frame as the first nucleotide sequence.

The complementary polypeptide whose amino acid sequence is thus determined may be obtained by diverse means such as, for example, chemical synthesis, derivation from a protein or larger polypeptide containing said amino acid sequence, or, when the second nucleic acid is DNA, inserting the second nucleotide sequence into a plasmid to form a recombinant DNA plasmid vector and transforming a unicellular organism therewith to produce a transformant unicellular organism biosynthesizing said complementary polypeptide.

The ascertainment of particular nucleotide sequences may be circumvented, in one aspect, by utilizing the relationships of amino acids having complementary hydropathies for substitutions as generally dictated by base-pairing nucleotide complementarity.

17 Claims, 7 Drawing Sheets

OTHER PUBLICATIONS

Biro, *Medical Hypotheses, 12: 203–226 (1983)*.
Segersteen et al., *Biochem. and Biophys. Research Comm.*, vol. 139, pp. 94–101 (1986).
Root-Bernstein, *J. Theor. Bio.*, vol. 94, pp. 885–894 (1982).
Blalock, et al., (1984), Biochem. Biophys. Res. Comm., 121:203–207.
Kyte, et al., (1982), J. Mol. Biol., 157:105–132.
Ramachandran, et al., (1980), *Proc. Natl. Acad. Sci. U.S.A.*, 77:3967–3970.
Yang et al., (1984), Proc. Natl. Acad. Sci. U.S.A., 81:2752–2756.
Nikaido, et al., (1984), Nature 311:631–635.
Tanaguchi, et al., (1983), Nature, 302:305–310.
Nisonoff, et al., (1984), The Antibody Molecule, pp. 29–39.
Schneider, et al., (1984), Nature, 311:675–678.
Ullrich, et al., (1984), Nature, 309:418–425.
Kaiser, et al., (1984), Science, 223:249–255.
Kaiser, et al., (1983), Proc. Natl. Acad. Sci. U.S.A., 80:1137–1143.
Hopp, et al., (1981), Proc. Natl. Acad. Sci. U.S.A., 78:3824–3828.
Nakanishi et al., (1979), Nature, 278:423–427.
Johnson, et al., (1982), J. Immunol., 129:2357–2359.
Smith, et al., (1982), Science 218:1311–1312.
Sege, et al., (1978), Proc. Natl. Acad. Sci. U.S.A., 75:2443–2447.
Devos, et al., (1983), Nucleic Acids Research, 11:4307–4322.
Patent Cooperation Treaty International Search Report, PCT/US86/00353.
Bost et al., (1985), Proc. Natl. Acad. Sci. USA, 82:1372–1375.
Dialog Search of the Scientific Literature.

Fig. 8

| EPIDERMAL GROWTH FACTOR | EPIDERMAL GROWTH FACTOR RECEPTOR | COMPLEMENTARY MESSAGE TO EPIDERMAL GROWTH FACTOR RECEPTOR |
|---|---|---|
| ASN SER TYR PRO GLY CYS PRO SER SER<br>AAU AGU UAU CCA GGA UGC CCA UCC UCA | 110<br>GLU LEU PRO MET ARG ASN LEU<br>GAG CTG CCC ATG AGA AAT TTA | 110<br>LEU ASP GLY TYR SER LEU ASN<br>CUC GAC GGG UAC UCU UUA AAU |
| 10<br>TYR ASP GLY TYR CYS LEU ASN GLY GLY<br>UAU GAU GGA UAC UGC CUC AAU GGU GGC | GLN GLU ILE LEU HIS GLY ALA VAL<br>GAG GAA ATC CTG CAT GGC GCC GTG | VAL LEU XXX ASP VAL PRO ARG HIS<br>GUC CUU XXX GAC GUA CCG CGG CAC |
| VAL CYS MET HIS ILE GLU SER LEU ASP<br>GUG UGC AUG CAU AUU GAA UCA CUG GAC | 120<br>ARG PHE SER ASN ASN PRO ALA LEU<br>CGG TTC AGC AAC AAC CCT GCC CTG | 120<br>ALA LYS SER LEU LEU GLY ARG ASP<br>GCC AAG UCG UUG UUG GGA CGG GAC |
| 30<br>SER TYR THR CYS ASN CYS VAL ILE GLY<br>AGC UAC ACA UGC AAC UGU GUU AUU GGC | 130<br>CYS ASN VAL GLU SER ILE GLN TRP<br>TGC AAC GTG GAG AGC ATC CAG TGG | THR LEU HIS LEU SER XXX VAL THR<br>ACG UUG CAC CUC UCG UAG GUC ACC |
| 40<br>TYR SER GLY ASP ARG CYS GLN THR ARG<br>UAU UCU GGG GAU CGA UGU CAG ACU CGA | 140<br>ARG ASP ILE VAL SER SER ASP PHE<br>CGG GAC ATA GTC AGC AGT GAC TTT | 140<br>ALA LEU TYR GLN SER SER LEU LYS<br>GCC CUG UAU CAG UCG UCA CUG AAA |
| 50<br>ASP LEU ARG TRP TRP GLU LEU ARG<br>GAC CUA CGA UGG UGG GAG CUG CGU | 150<br>LEU SER ASN MET SER MET ASP<br>CTC AGC AAC ATG TCG ATG GAC | 150<br>GLU SER LEU TYR SER TYR LEU<br>GAG UCG UUG UAC AGC UAC CUG |

Fig. 9A

| LIGAND | RECEPTOR | COMPLEMENTARY MESSAGE TO THE RECEPTOR | NUCLEOTIDE HOMOLOGY % | NUCLEOTIDE HOMOLOGY $P_a/10^{-5}$ | AMINO ACID HOMOLOGY % |
|---|---|---|---|---|---|
| EGF<br>11              16<br>ASP GLY TYR CYS LEU ASN<br>GAU GGA UAC UGC CUC AAU | EGF RECEPTOR<br>111             116<br>LEU PRO MET ARG ASN LEU<br>CTG CCC ATG AGA AAT TTA | EGF RECEPTOR COMPLEMENT<br>111             116<br>ASP GLY TYR SER LEU ASN<br>GAC GGG UAC UCU UUA AAU | 67 | 1.60 | 83 |
| 24              29<br>GLU SER LEU ASP SER TYR<br>GAA UCA CUG GAC AGC UAC | 149             154<br>LEU SER ASN MET SER MET<br>CTC AGC AAC ATG TCG ATG | 149             154<br>GLU SER LEU TYR SER TYR<br>GAG UCG UUG UAC AGC UAC | 78 | 0.178 | 83 |
| IL-2<br>34              39<br>LEU GLU HIS LEU LEU LEU<br>CUG GAG CAU UUA CUG CUG | IL-2 RECEPTOR<br>1              6<br>GLU LEU CYS ASP ASP ASP<br>GAG CTC TGT GAC GAT GAC | IL-2 RECEPTOR COMPLEMENT<br>1              6<br>LEU GLU THR LEU LEU LEU<br>CUC CAG ACA CUG CUA CUG | 61 | 4.26 | 83 |
| 2              6<br>TYR ARG MET GLN LEU<br>UAC AGG AUG CAA CUC | 18              22<br>MET ALA TYR LYS GLU<br>ATG GCC TAC AAG GAA | 18              22<br>TYR ARG MET PHE LEU<br>UAC CGG AUG UUC CUU | 67 | 3.56 | 80 |

Fig. 9B

| LIGAND | RECEPTOR | COMPLEMENTARY MESSAGE TO THE RECEPTOR | NUCLEOTIDE HOMOLOGY % | HOMOLOGY $P_a/10^{-5}$ | AMINO ACID HOMOLOGY % |
|---|---|---|---|---|---|
| TF | TF RECEPTOR | TF RECEPTOR COMPLEMENT | | | |
| 130              135<br>ILE PRO ILE GLY LEU LEU<br>AUC CCC AUA GGC UUA CUU | 219             214<br>TYR GLY GLY PRO ASN GLU<br>TAT GGT GGG CCT AAT GAG | 219             214<br>ILE PRO PRO GLY LEU LEU<br>AUA CCA CCC GGA UUA CUC | 61 | 4.26 | 83 |
| 235             239<br>VAL ASP GLU TYR LYS<br>GUA GAU GAA UAC AAG | 617             621<br>GLN LEU LEU SER PHE<br>CAA CTC CTT TCA TTT | 617             621<br>VAL ASP GLU SER LYS<br>GUU GAC GAA AGU AAA | 60 | 9.50 | 80 |
| 281             286<br>GLU PHE GLN LEU PHE SER<br>GAA UUC CAA CUA UUC AGC | 375             370<br>LEU LYS VAL ASN LYS SER<br>CTC AAG GTG AAT AAG AGC | 375             370<br>GLU PHE HIS LEU PHE SER<br>GAG UUC CAC UUA UUC UCG | 67 | 1.60 | 83 |
| 286             290<br>SER SER PRO HIS GLY<br>AGC UCU CCU CAU GGG | 326             330<br>SER SER GLY LEU PRO<br>TCA TCA GGA TTG CCT | 326             330<br>SER SER PRO ASN GLY<br>AGU AGU CCU AAC GGA | 60 | 9.50 | 80 |
| 324             328<br>ARG ASN LEU ARG GLU<br>CGG AAU CUA CGG GAA | 745             749<br>ALA ALA ASN ALA LEU<br>GCT GCA AAT GCC CTC | 745             749<br>ARG ARG LEU ARG GLU<br>CGA CGU UUA CGG GAG | 67 | 3.56 | 80 |
| 561             566<br>LEU LEU CYS LEU ASP GLY<br>UUG CUG UGC CUU GAU GGU | 559             564<br>GLU ASP THR ASP TYR PRO<br>GAG GAC ACA GAT TAT CCT | 559             564<br>LEU LEU CYS LEU ILE GLY<br>CUC CUG UGU CUA AUA GGA | 56 | 10.4 | 83 |
| 621             625<br>LEU PHE ARG SER GLU<br>UUG UUC CGG UCG GAA | 485             489<br>ASP LYS ALA VAL LEU<br>GAT AAA GCG GTT CTT | 485             489<br>LEU PHE ARG GLN GLU<br>CUA UUU CGC CAA GAA | 53 | 22.8 | 80 |

POLYPEPTIDES COMPLEMENTARY TO PEPTIDES OR PROTEINS HAVING AN AMINO ACID SEQUENCE OR NUCLEOTIDE CODING SEQUENCE AT LEAST PARTIALLY KNOWN AND METHODS OF DESIGN THEREFOR

RELATED APPLICATIONS

This is a continuation-in-part of co-pending U.S. patent application Ser. No. 708,001, filed Mar. 1, 1985.

BACKGROUND OF THE INVENTION

The present invention relates to methods for determining the structure of polypeptides having particular structural and biological activities and affinities.

The systematic design of pharmaceutical agents has currently reached a point where medicinal pharmacologists can often predict the activity of a particular pharmacologic agent from knowledge of its structure/function activity on a chemical level. This knowledge has been particularly useful in the design of new pharmacologic agents which are structurally related to a parent compound, but which exhibit new pharmacologic properties or activities.

For example, in the area of steroid biochemistry and design, the structure of various steroids has been modified in numerous ways to provide for enhanced or specialized activities. Another example of systematic drug design is in the medicinal chemistry of the synthetic penicillins: synthetic penicillins have now been designed which exhibit a number of activities not possessed by the non-synthetic penicillins. These improvements include a conference of oral activity, wide-spectrum activity, and activity against penicillinase-producing bacteria.

However, relatively little is known concerning the structure/function activities of macromolecular structures like proteins. For example, while it is known that antibodies bind to antigens, the underlying attractive interactions are incompletely understood. Even less is known about the underlying mechanism of the response to an antigenic challenge of producing a protein, in the form of an antibody, which is capable of binding an antigen.

Similarly, the interaction of peptide hormones with their hormone receptors is incompletely understood. It is known that in both the binding affinity of the peptide hormone for its receptor and the intrinsic activity of that bound hormone in "stimulating" the receptor, hormonal activity is expressed. From known structure/function relationships of non-protein hormones, it has been postulated that binding activity and intrinsic stimulating activity involve separate structural considerations. Certain chemical structures appear to provide for binding of the ligand, for example, a hormone, to its receptor. Yet other chemical structures appear to provide for "stimulation" of the receptor once the hormone is bound thereto.

Agents which possess binding activity, but not intrinsic stimulating activity, are known as "blockers" or antagonists in that they block the activity of the true hormone. An example of such a blocking agent is isoproterenol, a well-known catecholamine beta-blocker which was designed based on some knowledge of the structure/function relationships of catecholamines with their receptors. Similarly, agonists which both bind and activate hormonal receptors have been produced. No such structure/function relationships are entirely known for the polypeptide hormones. Thus, there is presently no way to accurately enable the systematic design of polypeptides capable of specifically interacting with a particular protein hormone receptor or with a particular polypeptide hormone.

All organisms having an intact immune system possess the biological capability to produce a class of very specialized proteins known as immunoglobulins. Immunoglobulins are produced by specialized cells of an immunocompetent organism in response to the presence of a molecule which is foreign to that organism. These foreign molecules are generally termed antigens. Antigens are operationally defined as being molecules capable of eliciting the formation of a complementary antibody in a given organism. A specific antibody thus formed is capable of binding to the antigen which stimulated its formation. The biological function of a specific antibody is to bind a foreign antigen and thus lead to its inactivation.

Scientists have succeeded in manipulating the immune system of various organisms to provide a vast array of antibodies which have proven useful in both therapeutic and diagnostic medicine. Recently, through the advent of hybridoma technology, science has developed a capability to produce monoclonal antibodies which will bind with specificity to a chosen molecular structure termed the determinant. The usefulness of such specific antibodies is immense, ranging from recent clinical experimentation which suggest an important future role in combating cancer to an everyday clinical role for antibodies in the detection of numerous disease states through blood examination.

One very interesting but largely theoretical application of antibody technology is in the area of anti-idiotypic antibodies. An anti-idiotypic antibody is a second antibody having binding capability for the idiotype or binding site of a first antibody. Such an anti-idiotypic antibody exhibits features in common with the antigen to which the first antibody binds. For example, if one generates antibodies against insulin and then proceeds to generate anti-idiotypic antibodies directed against the anti-insulin antibodies, a portion (idiotype) of the anti-idiotypic antibodies will exhibit insulin-like properties. This finding lends credence to the theory that the binding site of an antibody is a three-dimensional negative-image of the antigen and that an anti-idiotypic antibody to a first antibody is therefore a positive image of the original antigen. Such observations suggest that if such interactive structures could be designed and produced, a whole new array of biologically active substances, for instance, polypeptide hormones or receptors therefor, could be developed which exhibit a wide array of new and useful activities.

Although antibody technology has advanced rapidly, it still has fundamental technological limits. Science and medicine, for example, must still rely on an antibody-producing cell to generate the antibodies. Therefore, scientists have no direct control over antibody production. Such direct control would be a very important advantage. It would allow such advances as the production of man-made "antibodies" that could specifically interact with, or bind, not merely a selected molecule but a preselected portion of that molecule. The underlying basis of the attractive interaction between the antibody and antigen is as yet incompletely understood.

From the foregoing discussion, it is evident that antibody-producing cells have a mechanism to ascertain the chemical structure of an antigen and produce a complementary chemical structure in the form of an antibody. Such complementary results in a capability of binding to the antigenic structure. Prior to the advent of the present invention, in order to design or construct a protein structure complementary to, and thus capable of binding with another protein structure, a knowledge of the chemical interactions which underlie the binding phenomenon was necessary.

All proteins or peptides primarily are polymers of monomeric amino acid units. There are, in general, twenty different amino acids, each possessing a different chemical structure and thus different chemical and physical properties. For example some amino acids tend to be more hydrophobic in nature while others tend to be more hydrophilic in nature. Similarly, some amino acids tend to attract certain other amino acids while repelling yet other amino acids. Therefore, within any given protein, there are a variety of both attractive forces and repulsive forces exhibited by the individual amino acids of that protein. In addition to these interactive forces between amino acids of a given protein, there are also interactive forces between the amino acids and the surrounding environment. The latter forces depend on whether the protein resides, for example, in an aqueous or hydrophilic environment or in a non-aqueous or hydrophobic environment.

The interactive forces exhibited by the amino acids of a given protein are a major factor in determining the three-dimensional, or "ternary", structure of that protein. Therefore, in one view, certain regions within the protein are binding or attracting certain other regions of the same protein while other regions may be repelling certain regions within the protein. The net result is to give each protein a characteristic shape and, therefore, its functional activity.

Recently, there has been developed a means for characterizing amino acids in terms of hydropathy which reflects relative hydrophilicity and hydrophobicity (Kyte et al, (1982) J. Molec. Biol. Vol. 157, pp 105–132). A hydropathy scale was therein derived wherein the hydrophilic and hydrophobic properties of each of the twenty amino acid side-chains was taken into consideration. A computer program was utilized to continuously determine the average hydropathy within a polypeptide sequence of predetermined length. This study demonstrated that proteins have very distinct regions of hydrophobicity and hydrophilicity and that the intramolecular, in addition, of course, to internal disulfide bonding interaction of such regions, can account for the three dimensional structure of the proteins.

An even more recent study has suggested that amphiphilic protein structures, that is, protein structures which contain both hydrophilic and hydrophobic amino acids and regions, play an important role in maintaining the activity of both protein hormones and their receptors (Kaiser et al (1984) Science Vol. 223 pp 249–255). This study further suggests that amphiphilic structures in hormone receptors, for example, might be complementary as a mirror-image of amphiphilic structures in the hormones themselves. Therefore, the interaction between a hormone and its receptor could be mediated by a specific interaction between the amphiphilic structure of the hormone and a complementary amphiphilic structure of the receptor. One way in which this concept may be envisioned is to consider the model concept of a lock and its key, with the lock configuration representing the amphiphilic structure of the receptor and the configuration of the key representing the complementary amphiphilic structure of the hormone agent.

Accordingly, a means of systematically designing polypeptides which are capable of binding or interacting with known peptides, proteins or proteinaceous receptors would be of great utility. For example, practical knowledge concerning the design of receptor-interactive structures of proteinaceous hormones should lead to the development of whole new classes of synthetic hormones with greater specificity of activity. Conversely, one could design and produce polypeptides which are complementary to known proteinaceous hormones and therefore capable of binding to these hormones. Such designed polypeptides may be utilized, for example, to render the complementary hormone inactive.

Similarly, such knowledge of protein or peptide design could prove very significant for many fields of scientific research. For example, if a synthetic polypeptide which is complementary to a protein hormone is structurally analogous to the biological receptor for that hormone, then an antibody directed against that complementary protein should also bind the true hormone receptor. Such antibodies would be useful in studying and isolating specific hormone receptors or portions thereof to thereby lead to an even greater understanding of hormone-receptor interactions. In addition, a synthetic protein or peptide which is complementary to a particular protein should be useful in the crystallization of that protein for the purpose, for example, of probing the protein structure through x-ray crystallography. Further, detoxifying polypeptides could be designed to tightly and specifically bind to toxic peptides found in nature and sometimes ingested.

The above illustrations are just a few of the numerous possible applications that synthetic protein or peptide design capabilities would enable. The ability to systematically design a polypeptide that will interact with or bind to known proteins, the design being based on structural considerations of the known protein, would clearly constitute a scientific breakthrough of major proportions in the field of peptide and/or chemistry and medicinal pharmacology.

For purposes of clarification and consistency, the following terms are defined as to their general meaning herein.

The term antiparallel, referring to nucleic acid pairings, indicates a directionality as to the paired nucleic acids. The original nucleic acid may be in a 5' to 3' direction where the 5' and 3' refer to positions on the sugar moieties involved in nucleotide coupling. The second nucleic acid strand base-paired or complementary to the original nucleic acid strand lies in a 3' to 5' direction when linearly aligned with the original strand having a 5' to 3' directionality.

The coding nucleic acid contains the sequence of nucleotide triplets (codons) specifying a sequence of amino acids when read in a 5' to 3' direction. The non-coding (complementary) nucleic acid (or nucleic acid strand) is complementary to the coding nucleic acid (or nucleic acid strand), the strands lying or base-pairing in an antiparallel direction.

The term hydropathic complementarity, referring to the hydropathic scores (a relative measure of hydrophilicity and hydrophobicity) of amino acids indicates a low hydropathy corresponding to a high hydropathy and vice versa.

In referring to structures comprising amino acids, they are generally referred to as peptides, polypeptides or proteins, this order designating an increase in size between, for example, dipeptides, oligopeptides, and proteins containing many hundred of amino acids.

The term complementary, or complement, as used herein has a meaning based upon its context of usage. For example, complementary bases or nucleotides are those characteristically forming hydrogen bonds (G-C and A-T or A-U), complementary codons nucleic acids or strands thereof are hydrogen bonded polynucleotide components of a double nucleic acid strand such of that in the classically defined double helix for example complementary amino acids usually having hydropathic complementarity are those directed by members of a pair of complementary codons.

Complementary peptides or polypeptides and their related original peptide or protein are a pair of peptides directed by complementary nucleotide or amino acid sequences, and characteristically have a binding affinity between members of a pair. Polypeptides complementary to a peptide or at least a portion of a protein, for example, have a binding affinity for the peptide or protein portion. While peptide binding affinities are incompletely understood, they may, in part at least, be explained by the concept of amphiphilic secondary structure described by Kaiser et al (Science (1984) Vol. 223 pp. 249–255).

SUMMARY OF THE INVENTION

A method for determining the amino acid sequence of a polypeptide complementary to at least a portion of an original peptide or protein has not, before now, been discovered. In one aspect the method involves: (a) deriving a first nucleotide sequence of a first nucleic acid potentially coding for the biosynthesis of at least a portion of the original peptide or protein; (b) determining a second nucleotide sequence of a second nucleic acid which base-pairs with the first nucleotide sequence of the first nucleic acid, the first and second nucleic acids pairing in antiparallel directions; and (c) determining the amino acid sequence of the complementary polypeptide by the second nucleotide sequence when read in the same reading frame as the first nucleotide sequence.

The complementary polypeptide whose amino acid sequence is thus determined may be obtained by diverse means such as, for example, chemical synthesis, derivation from a protein or larger polypeptide containing said amino acid sequence, or, when the second nucleic acid is DNA, inserting the second nucleotide sequence into a plasmid to form a recombinant DNA plasmid vector and transforming a unicellular organism therewith to produce a transformant unicellular organism biosynthesizing said complementary polypeptide.

In one aspect the present invention is related to the design and production of polypeptides capable of specifically interacting with selected target peptide structures of known amino acid sequence.

BRIEF DESCRIPTION OF THE DRAWINGS

FIG. 8 depicts nucleotide and amino acid sequences for epidermal growth factor (EGF), EGF receptor. The nucleotide sequence complementary to the nucleotide sequence for EGF receptor and the amino acid sequence coded by the complementary nucleotide sequence when read in the 3' to 5' direction are also depicted. For the sequences of EGF and EGF receptor, the lower numbered positions represent the 5' nucleotide direction and the amino-terminal amino acid direction. For the sequences of the complementary message to the EGF receptor, the lower numbered positions represent the 3' nucleotide direction and the amino-terminal amino acid direction. Homologous sequences are boxed.

FIGS. 9A and 9B depict certain nucleotide and amino acid sequences of: peptide hormones [EGF, interleukin-2 (IL-2) and transferrin (TF)]; peptide hormone receptors [EGF receptor, IL-2 receptor and TF receptor]; and complementary message to the receptors. For the peptide hormone and receptor sequences, the lower numbered positions represent the 5' nucleotide direction and the amino-terminal amino acid direction. For the sequences of the complementary message, the lower numbered positions represent the 3' nucleotide direction and the amino-terminal amino acid direction. The complementary nucleotide was read in the 3' to 5' direction to produce the corresponding amino acid sequence.

DETAILED DESCRIPTION OF THE PREFERRED EMBODIMENTS

Figure 1:
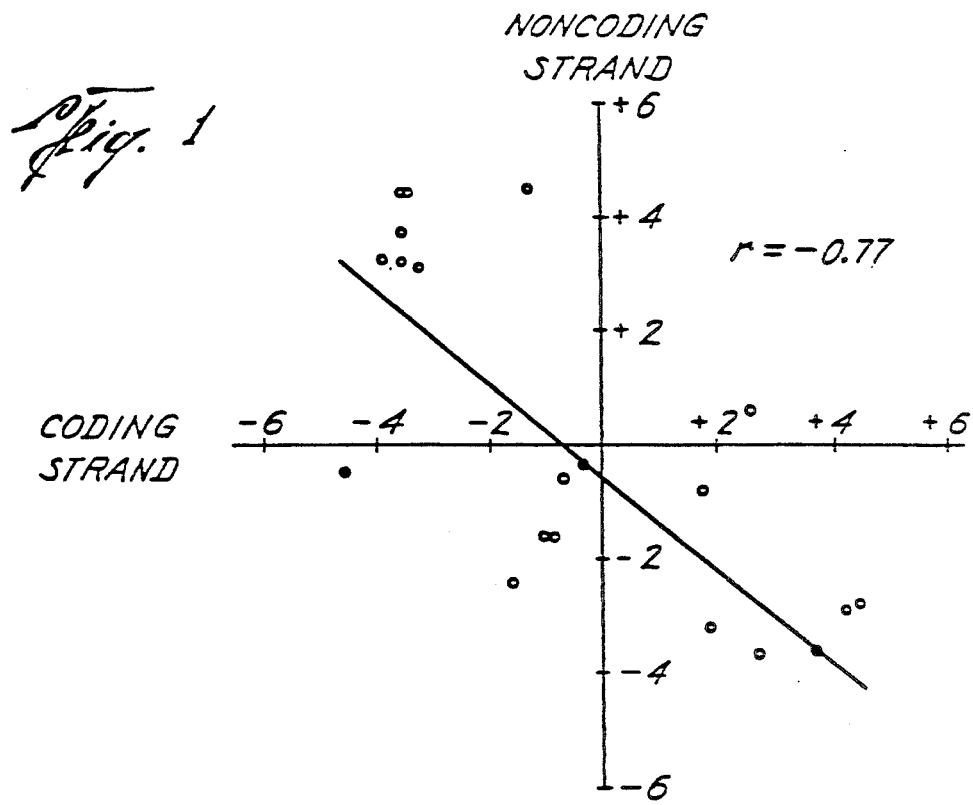
FIG. 1 graphically depicts the relationship of hydropathic scores of amino acids specified by a nucleotide strand containing coding information and its anti-parallel base-paired complementary or noncoding nucleotide strand. The triplet nucleotide code of each strand was read in the 5' to 3' direction. The hydropathic scores of the coded amino acids are plotted against the average hydropathic scores of complementary coded amino acids.

The interactions of biologically significant molecules are a basis of intercellular and interorgan communications. When the particular biologically significant communicating molecules are, for example, peptide hormones and peptide-containing cellular receptors therefor, a basis and rational explanation for their communicative interactions have long been sought.

A previously unobserved and fundamental relationship has been found, as described herein, to exist between antiparallel base-pairing strands of nucleic acids. In one aspect, this relationship may give rise to pairs of peptides where each member of a particular pair has an affinity for the other member. The basic relationship is demonstrated in Table 1 where the various codons and their complementary (i.e. base pairing) codons are presented. The codons of a coding strand, (e.g. that strand containing the coding information describing an amino acid sequence) are represented as being read from left to right (the 5' to 3' direction). The codons of the complementary (i.e. noncoding) antiparallel base-paired strand are also read from in the 5' to 3' direction. Noncoding and coding nucleic acid strands pair when lying in an antiparallel direction (e.g. coding strand from left to right being 5' to 3' and noncoding strand from left to right being 3' to 5') so that the paired codons are viewed lying in an opposite observable direction (e.g. left to right vs. right to left) when read in the 5' to 3' direction. The codons given in Table 1 have been grouped suggestively by hydropathy as defined by Kyte et al. This specific grouping is used for illustrative purposes only and should not be viewed as restrictive of the scope of the present invention. As can be seen in Table 1, the complementary codons pairing with codons for the hydrophobic (high hydropathy) amino acids exhibit a tendency to code for hydrophilic (low hydropathy) amino acids. The reciprocal situation is shown with codons of the hydrophilic amino acids. For the slightly hydrophilic amino acids (slightly negative hydropathy), similar amino acids are coded for by the complementary codons. These results are shown in graphical form in FIG. 1. This relationship has great biological significance as described hereinafter.

TABLE 1

AMINO ACIDS WHOSE CODONS ARE COMPLEMENTARY TO THOSE OF THE:

| Coding Strand | | Noncoding Strand | |
|---|---|---|---|
| Codon | Amino Acid | Codon | Amino Acid |
| (1) Hydrophobic Amino Acids | | | |
| AUU | Isoleucine | AAU | Asparagine |
| AUC | Isoleucine | GAU | Aspartic acid |
| AUA | Isoleucine | UAU | Tyrosine |
| GUU | Valine | AAC | Asparagine |
| GUC | Valine | GAC | Aspartic acid |
| GUG | Valine | CAC | Histidine |
| GUA | Valine | UAC | Tyrosine |
| CUU | Leucine | AAG | Lysine |
| CUC | Leucine | GAG | Glutamic acid |
| CUG | Leucine | CAG | Glutamine |
| UUG | Leucine | CAA | Glutamine |
| UUU | Phenylalanine | AAA | Lysine |
| UUC | Phenylalanine | GAA | Glutamic acid |
| UGU | Cysteine | ACA | Threonine |
| UGC | Cysteine | GCA | Alanine |
| AUG | Methionine | CAU | Histidine |
| GCG | Alanine | CGC | Arginine |
| GCU | Alanine | AGC | Serine |
| GCC | Alanine | GCC | Glycine |
| GCA | Alanine | UGC | Cysteine |
| (2) Hydrophilic Amino Acids | | | |
| CGC | Arginine | GCG | Alanine |
| CGU | Arginine | ACG | Threonine |
| CGA | Arginine | UCG | Serine |
| AGA | Arginine | UCU | Serine |
| CGG | Arginine | CCG | Proline |

TABLE 1-continued

AMINO ACIDS WHOSE CODONS ARE COMPLEMENTARY TO THOSE OF THE:

| Coding Strand | | Noncoding Strand | |
|---|---|---|---|
| Codon | Amino Acid | Codon | Amino Acid |
| AGG | Arginine | CCU | Proline |
| AAG | Lysine | CUU | Leucine |
| AAA | Lysine | UUU | Phenylalanine |
| AAU | Asparagine | AUU | Isoleucine |
| AAC | Asparagine | GUU | Valine |
| GAU | Aspartic acid | AUC | Isoleucine |
| GAC | Aspartic acid | GUC | Valine |
| CAA | Glutamine | UUG | Leucine |
| CAG | Glutamine | CUG | Leucine |
| GAG | Glutamic acid | UUG | Leucine |
| GAA | Glutamic acid | UUC | Phenylalanine |
| CAC | Histidine | GUG | Valine |
| CAU | Histidine | AUG | Methionine |
| (3) Slightly Hydrophilic Amino Acid | | | |
| GGU | Glycine | ACC | Threonine |
| GGA | Glycine | UCC | Serine |
| GGG | Glycine | CCC | Proline |
| GGC | Glycine | GCC | Alanine |
| ACC | Threonine | GGU | Glycine |
| ACU | Threonine | AGU | Serine |
| ACG | Threonine | CGU | Arginine |
| ACA | Threonine | UGU | Cysteine |
| UGG | Tryptophan | CCA | Proline |
| UCC | Serine | GGA | Glycine |
| AGU | Serine | ACU | Threonine |
| UCG | Serine | CGA | Arginine |
| UCU | Serine | AGA | Arginine |
| AGC | Serine | GCU | Alanine |
| UAU | Tyrosine | AUA | Isoleucine |
| UAC | Tyrosine | GUA | Valine |
| CCC | Proline | GGG | Glycine |
| CCA | Proline | UGG | Tryptophan |
| CCU | Proline | AGG | Arginine |
| CCG | Proline | CGG | Arginine |

The paired codons (nucleotide triplets) in Table 1 result from comparing hypothetical coding nucleic acid strands (RNA in this case) and non-coding nucleic acid strands (RNA paired in an antiparallel direction. Both strands were then read in the 5' to 3' direction and in the same reading frame to obtain the original codons and their complementary (base-paired) codons.

Of the possible 20 complementary codons for the hydrophobic amino acid-coding codons, only two (GCA and UCG) code for hydrophobic amino acids. Of the possible 18 complementary codons for the hydrophilic amino acid-coding codons, 13 coded for hydrophobic amino acids and 5 coded for slightly hydrophilic amino acids.

Of the possible 20 complementary codons for the slightly hydrophilic amino acid coding codons, 10 coded for slightly hydrophobic amino acids, 5 coded for strongly hydrophilic amino acids and 5 coded for strongly hydrophobic amino acids, the net comparative effect being little change in hydropathic character.

Table 2 lists the coded amino acids and their respective complementarily coded amino acids of Table 1 and includes their hydropathic scores (Kyte et al, 1982).

TABLE 2

HYDROPATHIC SCORES OF AMINO ACIDS AND THEIR COMPLEMENTS AS DESCRIBED IN TABLE 1

| AMINO ACIDS | SCORE | COMPLE-MENTS | SCORES | AVERAGE SCORE |
|---|---|---|---|---|
| ILE | +4.5 | ASN | −3.5 | |
| | | ASP | −3.5 | |
| | | TYR | −1.3 | −2.8 |
| VAL | +4.2 | ASN | −3.5 | |
| | | ASP | −3.5 | |

TABLE 2-continued

HYDROPATHIC SCORES OF AMINO ACIDS AND THEIR COMPLEMENTS AS DESCRIBED IN TABLE 1

| AMINO ACIDS | SCORE | COMPLEMENTS | SCORES | AVERAGE SCORE |
|---|---|---|---|---|
| | | HIS | −3.2 | |
| | | TYR | −1.3 | −2.9 |
| LEU | +3.7 | LYS | −3.9 | |
| | | GLU | −3.5 | |
| | | GLN | −3.5 | −3.6 |
| PHE | +2.7 | LYS | −3.9 | |
| | | GLU | −3.5 | −3.7 |
| CYS | +2.5 | THR | −0.7 | |
| | | ALA | +1.8 | +0.6 |
| MET | +1.9 | HIS | −3.2 | |
| ALA | +1.8 | ARG | −4.5 | |
| | | SER | −0.9 | |
| | | GLY | −0.4 | |
| | | CYS | +2.5 | −0.8 |
| ARG | −4.5 | ALA | +1.8 | |
| | | THR | −0.7 | |
| | | SER | −0.9 | |
| | | PRO | −1.6 | −0.5 |
| LYS | −3.9 | LEU | +3.7 | |
| | | PHE | +2.7 | +3.2 |
| ASN | −3.5 | ILE | +4.5 | |
| | | VAL | +4.2 | +4.4 |
| ASP | −3.5 | ILE | +4.5 | |
| | | VAL | +4.2 | +4.4 |
| GLN | −3.5 | LEU | +3.7 | +3.7 |
| GLU | −3.5 | LEU | +3.7 | |
| | | PHE | +2.7 | +3.2 |
| HIS | −3.2 | VAL | +4.2 | |
| | | MET | +1.9 | +3.1 |
| GLY | −0.4 | THR | −0.7 | |
| | | SER | −0.9 | |
| | | PRO | −1.6 | |
| | | ALA | +1.8 | −0.1 |
| THR | −0.7 | GLY | −0.4 | |
| | | SER | −0.9 | |
| | | ARG | −4.5 | |
| | | CYS | +2.5 | −0.8 |
| TRP | −0.9 | PRO | −1.6 | −1.6 |
| SER | −0.9 | GLY | −0.4 | |
| | | THR | −0.7 | |
| | | ARG | −4.5 | |
| | | ALA | +1.8 | −1.6 |
| TYR | −1.3 | ILE | +4.5 | |
| | | VAL | +4.2 | +4.4 |
| PRO | −1.6 | GLY | −0.4 | |
| | | TRP | −0.9 | |
| | | ARG | −4.5 | −2.5 |

As shown in Table 2 and graphically illustrated in FIG. 1, a general relationship exists as exemplified by sets of amino acids. For example, a first set of amino acids directed (i.e. coded for) by a first group of codons and a second set (complementarily coded) of amino acids are directed by a second group of codons complementary to the first group of codons. A relationship between the first set of amino acids and the second set of amino acids is found which may be characterized as hydropathically inverse. In one instance, complementarily coded hydrophilic (low hydropathy) amino acids are directed by codons complementary to those coding for the hydrophobic (high hydropathy) amino acids. This relationship may be termed hydropathic complementarity.

FIG. 1 shows a plot of data from Table 2 showing the hydropathic scores of the amino acids directed by codons of a coding nucleic acid strand versus the average hydropathic scores of the amino acids complementarily directed by the codons of the the complementary noncoding strand. A linear regression analysis of this data results in a correlation coefficient of −0.77. A similar pattern is observed when calculated by another hydropathic scoring system which has somewhat different values for tryptophan, tyrosine, glutamine and asparagine (data not shown, Hopp et al, Proc. Natl. Acad. Sci. (1981) Vol. 78 pp. 3824-3828). Thus the noncoding strand-directed amino acid hydropathic scores tend to be inversely related to the coding strand amino acid hydropathic scores and this relationship is not random and could be found with any scoring system reflecting amino acid properties reflecting hydrophobic and hydrophilic tendencies, alone or in combination with other physical properties of amino acids.

Interestingly, a similar relationship also arises when the complementary codons are read in the 3' to 5' direction. The coding relationships of complementary codons read in the 3' to 5' direction are shown in Table 3.

TABLE 3

AMINO ACIDS WHOSE CODONS ARE COMPLEMENTARY TO THOSE OF:

| Coding Strand | | Noncoding Strand | |
|---|---|---|---|
| Codon | Amino Acid | Codon | Amino Acid |
| (1) Hydrophobic Amino Acids | | | |
| AUA | Isoleucine | UAU | Tyrosine |
| GUU | Valine | CAA | Glutamine |
| GUC | Valine | CAG | Glutamine |
| GUG | Valine | CAC | Histidine |
| GUA | Valine | CAU | Histidine |
| UUA | Leucine | AAU | Asparagine |
| UUG | Leucine | AAC | Asparagine |
| CUU | Leucine | GAA | Glutamic Acid |
| CUC | Leucine | GAG | Glutamic Acid |
| CUA | Leucine | GAU | Aspartic Acid |
| CUG | Leucine | GAC | Aspartic Acid |
| UUU | Phenylalanine | AAA | Lysine |
| UUC | Phenylalanine | AAG | Lysine |
| UGU | Cysteine | ACA | Threonine |
| UGC | Cysteine | ACG | Threonine |
| AUG | Methionine | UAC | Tyrosine |
| GCU | Alanine | CGA | Arginine |
| GCC | Alanine | CGG | Arginine |
| GCA | Alanine | CGU | Arginine |
| GCG | Alanine | CGC | Arginine |
| (2) Hydrophilic Amino Acids | | | |
| CGU | Arginine | GCA | Alanine |
| CGC | Arginine | GCG | Alanine |
| CGA | Arginine | GCU | Alanine |
| CGG | Arginine | GCC | Alanine |
| AGA | Arginine | UCU | Serine |
| AGG | Arginine | UCC | Serine |
| AAA | Lysine | UUU | Phenylalanine |
| AAG | Lysine | UUC | Phenylalanine |
| AAU | Asparagine | UUA | Leucine |
| AAC | Asparagine | UUG | Leucine |
| GAU | Aspartic Acid | CUA | Leucine |
| GAC | Aspartic Acid | CUG | Leucine |
| CAA | Glutamine | GUU | Valine |
| CAG | Glutamine | GUC | Valine |
| GAG | Glutamic Acid | CUC | Leucine |
| GAA | Glutamic Acid | CUU | Leucine |
| CAC | Histidine | GUG | Valine |
| CAU | Histidine | GUA | Valine |
| (3) Slightly Hydrophilic Amino Acids | | | |
| GGU | Glycine | CCA | Proline |
| GGC | Glycine | CCG | Proline |
| GGA | Glycine | CCU | Proline |
| GGG | Glycine | CCC | Proline |
| ACC | Threonine | UGG | Tryptophan |
| ACG | Threonine | UCG | Cysteine |
| ACA | Threonine | UGU | Cysteine |
| UGG | Tryptophan | ACC | Threonine |
| UCU | Serine | AGA | Arginine |
| UCC | Serine | AGG | Arginine |
| UCA | Serine | AGU | Serine |
| UCG | Serine | AGC | Serine |
| AGU | Serine | UCA | Serine |
| AGC | Serine | UCG | Serine |
| UAU | Tyrosine | AUA | Isoleucine |
| UAC | Tyrosine | AUG | Methionine |

TABLE 3-continued

| AMINO ACIDS WHOSE CODONS ARE COMPLEMENTARY TO THOSE OF: | | | |
|---|---|---|---|
| Coding Strand | | Noncoding Strand | |
| Codon | Amino Acid | Codon | Amino Acid |
| CCU | Proline | GGA | Glycine |
| CCC | Proline | GGG | Glycine |
| CCA | Proline | GGU | Glycine |
| CCG | Proline | GGC | Glycine |

As shown in Table 3, of the 20 possible codons complementary to the codons for hydrophobic amino acids, when read in the 3' to 5' direction, none coded for hydrophobic amino acids, 16 coded for hydrophilic amino acids and 4 (UAU, ACA, ACG and UAC) coded for slightly hydrophilic amino acids.

Of the 18 possible codons complementary to the codons for the strongly hydrophilic amino acids, when read in the 3' to 5' direction, none coded for strongly hydrophilic amino acids, 16 for hydrophobic amino acids and two (UCU and UCC) for slightly hydrophilic amino acids.

Table 4 lists the hydropathic scores of amno acids and their complements (i.e. amino acids complementarily coded or coded by respective complementary codons) described in Table 3.

TABLE 4

| HYDROPATHIC SCORES OF AMINO ACIDS AND THEIR COMPLEMENTS AS DESCRIBED IN TABLE 3 | | | |
|---|---|---|---|
| AMINO ACID | SCORE | COMPLEMENTS | SCORES |
| ILE | +4.5 | TYR | −1.3 |
| VAL | +4.2 | GLN | −3.5 |
| | | HIS | −3.2 |
| LEU | +3.7 | ASN | −3.5 |
| | | GLU | −3.5 |
| | | ASP | −3.5 |
| PHE | +2.7 | LYS | −3.9 |
| CYS | +2.5 | THR | −0.7 |
| MET | +1.9 | TYR | −1.3 |
| ALA | +1.8 | ARG | −4.5 |
| ARG | −4.5 | ALA | +1.8 |
| | | SER | −0.9 |
| LYS | −3.9 | PHE | +2.7 |
| ASN | −3.5 | LEU | +3.7 |
| ASP | −3.5 | LEU | +3.7 |
| GLN | −3.5 | VAL | +4.2 |
| GLU | −3.5 | LEU | +3.7 |
| HIS | −3.2 | VAL | +4.2 |
| GLY | −0.4 | PRO | −1.6 |
| THR | −0.7 | TRP | −0.9 |
| | | CYS | +2.5 |
| TRP | −0.9 | THR | −0.7 |
| SER | −0.9 | ARG | −4.5 |
| | | SER | −0.9 |
| TYR | −1.3 | ILE | +4.5 |
| | | MET | +1.9 |
| PRO | −1.6 | GLY | −0.4 |

Of the possible complementary codons to the codons coding for slightly hydrophilic amino acids, when read in the 3' to 5' direction, 14 code for slightly hydrophilic amino acids, 2 (ACA and ACG) code for strongly hydrophilic amino acids and 4 (UCG, UGU, AUA and AUG) code for hydrophobic amino acids. The net effect here being little change in the average hydropathic character of the noncoding strand amino acids.

Figure 2:
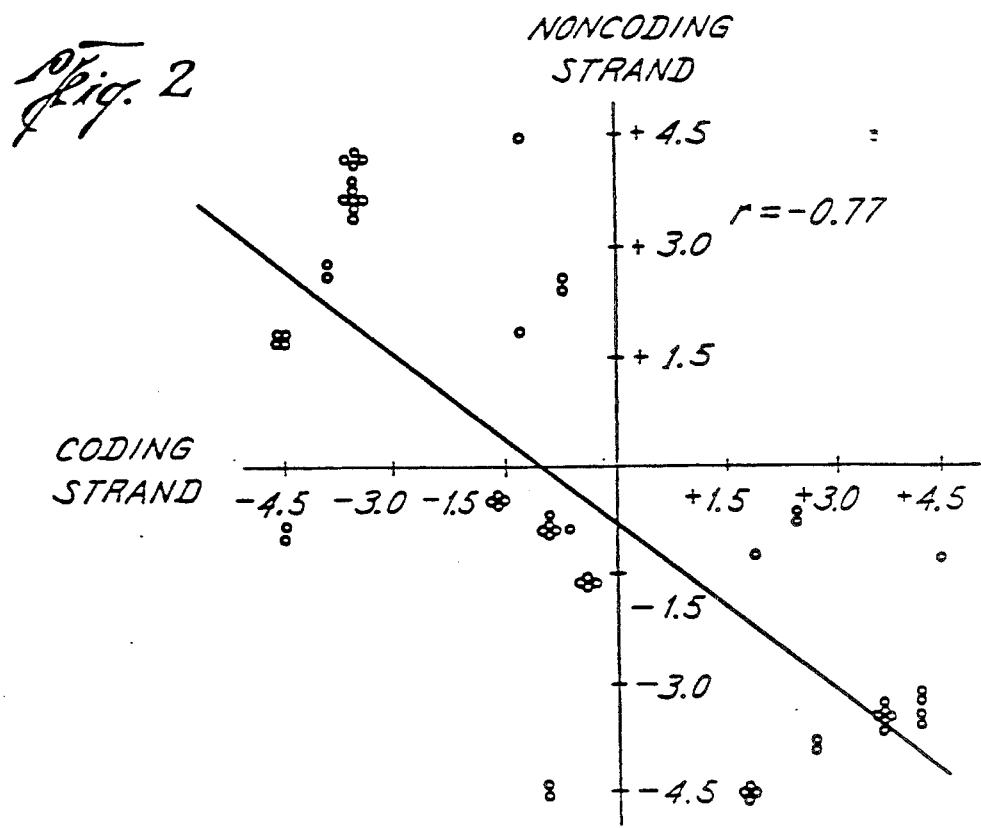
FIG. 2 graphically depicts the relationship of hydropathic scores of amino acids coded by a coding nucleotide strand and its antiparallel base-paired non-coding nucleotide strand. The triplet nucleotide code of the coding strand was read in the 5' to 3' direction, while that of the noncoding strand, in the 3' to 5' direction. The hydropathic scores of the coded amino acids are plotted against the hydropathic scores of complementarily coded amino acids.

FIG. 2 shows a plot of the hydropathic scores of the coding strand amino acids versus the hydropathic scores of the noncoding strand amino acids. A linear regression analysis of this data results in a correlation coefficient of −0.77. Thus, as was the case for the 5' to 3' direction, in the 3' to 5' direction, the noncoding strand amino acid hydropathic scores are inversely related to those of the coding strand and this relationship is not random.

These relationships of information contained in the genetic code demonstrate a hydropathic complementarity of amino acids. Codons, when read in the 5' to 3' direction, for hydrophilic and hydrophobic amino acids were generally complemented by codons for hydrophobic and hydrophilic amino acids, respectively. The average tendency of codons for "uncharged" (slightly hydrophilic) amino acids was to be complemented by codons for "uncharged" amino acids.

As demonstrated by these observations an almost identical pattern results when the complementary nucleotide codon is read in the 3' to 5' rather than the 5' to 3' direction. Since, regardless of the reading direction, the second nucleotide of the complementary codon never changes, this second nucleotide of the triplet codon is the principal determinant for the hydropathic complementarity of amino acids which are specified by complementary codons. This seems to largely result from the fact that the preponderance (6 out of 7) of hydrophilic amino acids have adenine as their second nucleotide codon while the complementary nucleotide uridine, is the second nucleotide of the triplet codon for most (5 of 7) hydrophobic amino acids. One of the 2 exceptions to the above in the hydrophobic group (alanine) does not seriously vitiate the above generality as it has a second base, cytosine, while the second base for the single exception in the hydrophilic group (arginine) has a second base, guanine. Hence, there is a virtually perfect interchange of hydrophobic and hydrophilic amino acids whether the complementary codon is read in the 5' to 3' or 3' to 5' direction. Of the six uncharged (slightly hydrophilic) amino acids with the exception of tyrosine, the second base of the respective codons is either a G or C. Hence, the codons for this group will usually result in a similar type of amino acid regardless of the direction in which the complementary codon is read.

Table 5 lists amino acids whose codons contain a particular second (middle) base.

TABLE 5

| AMINO ACIDS HAVING A PARTICULAR SECOND BASE IN THEIR CODONS | |
|---|---|
| SECOND BASE OF RNA CODON | AMINO ACIDS |
| U | ILE |
| | VAL |
| | LEU |
| | PHE |
| | MET |
| A | LYS |
| | ASN |
| | ASP |
| | GLN |
| | GLU |
| | HIS |
| | TYR |
| G | CYS |
| | ARG |
| | GLY |
| | TRP |
| | SER |
| C | THR |
| | SER |
| | PRO |
| | ALA |

The group of amino acids (U group) directed by a uridine second base have a complementarily coded group of amino acids (A group) coded by an adenine second base, and vice versa. The cytosine and guanine directed groups (C group and G group respectively) have the same relationship.

Table 6 lists the hydropathic scores of amino acids directed by codons having a particular second base and, for convenience separately shows corresponding scores for the complementarily coded amino acids (complement). Again, the hydropathically complementary relationship is illustrated.

TABLE 6

HYDROPATHIC SCORES OF AMINO ACIDS AND THEIR COMPLEMENTS BASED ON GROUPINGS SHOWN IN TABLE 5

| Second Base Group | | | Average Hydropathic Scores | |
|---|---|---|---|---|
| | | | Coded | Complement |
| U | ILE | +4.5 | | |
|   | VAL | +4.2 | | |
|   | LEU | +3.7 | | |
|   | PHE | +2.7 | | |
|   | MET | +1.9 | +3.4 | −3.2 |
| A | LYS | −3.9 | | |
|   | ASN | −3.5 | | |
|   | ASP | −3.5 | | |
|   | GLN | −3.5 | | |
|   | GLU | −3.5 | | |
|   | HIS | −3.2 | | |
|   | TYR | −1.3 | −3.2 | +3.4 |
| G | CYS | −2.5 | | |
|   | ARG | −4.5 | | |
|   | GLY | −0.4 | | |
|   | TRP | −0.9 | | |
|   | SER | −0.9 | −0.8 | −0.4 |
| C | THR | −0.7 | | |
|   | SER | −0.9 | | |
|   | PRO | −1.6 | | |
|   | ALA | +1.8 | −0.4 | −0.8 |

Clearly, from Tables 2, 4 and 6 it can be seen that peptides and their complements are related by a general inversion of hydropathic nature on an amino acid by amino acid basis, when the sequences are aligned in a parallel or anti-parallel manner depending on the method of generation. demonstrated by utilization of the specific codon relationships shown in Table 1 and Table 3 are special cases of a more generally defined method to generate complementary peptides.

When nucleic acid sequences are not known, the general methods based on second base complementarity or hydropathic inversion may be used to generate homologs of the specifically preferred complementary peptides. For example, when an amino acid sequence but not the particular codons for all or a portion of a protein or peptide is known, a complementary peptide may be designed based upon the general relationships shown in Table 6. For an amino acid in the original protein or peptide sequence having a second codon base of uridine (U group amino acid), an amino acid for the A group is substituted and vice versa. For an amino acid in the protein or peptide sequence having a second codon base of cytosine (C group), an amino acid from the guanine (G group) is substituted and vice versa. After these substitutions the sequence of amino acids thus obtained will be complementary to repective portions of the original peptide or protein.

Tables 1, 3 and 6 can be used in a general manner when the nucleic acid sequences are not known. In such cases, for an amino acid in the original peptide or protein sequence, an amino acid is substituted from the corresponding set of non-coding strand amino acids. After these substitutions, the sequence of amino acids thus obtained will be complementary to the respective portions of the original peptide or protein.

As a further extension of the principles of the present invention, the specific directionality of the complementary amino acid sequence may not be critical. As is clear to one skilled in the art upon study of the entire description presented herein, the juxtaposition of amino acids in construction of complementary polypeptide may be directionally oriented in either of two ways. Relative to the amino acid sequence directing positioning of amino acids having particular hydropathic character, the amino terminal and carboxy terminal directions are interchangeable, both constructions giving rise to complementary polypeptides. In simpler form, for one example, if the amino terminal end of a particular amino acid sequence contains a valine (second codon base=U), then a complementary amino acid sequence would contain, at the amino terminal end or the carboxy terminal end, an amino acid having a second codon base A (LYS, ASN, ASP, GLN, GLU, HIS, or TYR), using the general method based on Table 6.

The genetic code may have arisen during evolution as a result of the chemical similarity of anticodonic bases and their respective amino acids. Perhaps this similarity resulted in the patterns observed herein. A functional and evolutionary advantage to this phenomenon may reside in the fact that the second base of codons for hydropathically similar amino acids is the same. Perhaps, prior to the advent of the directionality of nucleic acid reading, an amino acid from the same hydropathic group would be present and thus the resulting peptides or proteins would be grossly similar in conformation, whether nucleic acids were read 5' to 3' or 3' to 5'.

The present invention relates, in a major aspect, to the discovery that polypeptides complementary to at least a portion of an original peptide or protein having known amino acid sequence or nucleotide coding sequence and has binding affinity to the original peptide or protein may be designed and obtained. If the amino acid sequence of at least a portion (for example four to five amino acids) of an original peptide or protein is known, information of that sequence may be used in several ways to determine the design of a complementary polypeptide.

A preferred way of designing a complementary polypeptide utilizes the amino acid relationships delineated in Table 3. Accordingly, for any position of isoleucine in an ascertained amino acid sequence of all or part of the original peptide or protein, substitute tyrosine. As one further example, for each valine substitute glutamine or histidine. The residual 18 amino acids are also substituted according to the relationships illustrated in Table 3. As shown subsequently herein (Examples 2A, 2B and 2C, for example,) when peptide hormone-receptor site amino acid sequences are utilized as original peptides or proteins, statistically significant and unique codon directions are given for portions of the peptide hormones which characteristically bind at those receptor sites and are thus complementary thereto. By further examination of Examples 2A, 2B and 2C and also of FIGS. 8, 9A and 9B, it is shown that more preferable substitutions were made therein for specific amino acids based on known nucleotide sequence, for example serine was substituted for arginine and serine or cysteine was substituted for threonine.

Another preferred method of designing complementary polypeptides involves usage of the amino acid relationships presented in Table 1. Accordingly, however, an amino acid sequence of the original peptide, protein or portion thereof desired is read from the carboxy terminal direction. This carboxy terminal direction is to substitutingly correspond (i.e. give the directions for amino acid emplacement) to the amino terminal direction of the complementary polypeptide. Once this reversal of order is attained, substitutions may be made according to the amino acid relationships shown in Table 1. For example, in place of each isoleucine is substituted a tyrosine, asparagine or aspartic acid. Further substitutions for the other 19 amino acids may take place as directed by the amino acid relationships of Table 1.

As subsequently demonstrated in Examples 1A to 1H, when polypeptides complementary to gamma endorphin and ACTH were designed following a preferred variant of the latter method and obtained, specific amino acid substitutions based on known nucleotide sequences were made. For example, for valine, aspartic acid or histidine was substituted; for leucine-lysine or glumatic acid was substituted; for phenylalanine-glumatic acid; for arginine-alanine or proline; for lysine-leucine; for histidine-valine; for glycine-proline or alanine; for threonine-glycine or arginine; for serine-glycine, arginine or alanine; for tyrosine-valine; and for proline-glycine or arginine.

Another preferred method to select a specific set of complementary amino acids from the general second base grouping is given below. For each amino acid, generate a list of all of the possible complementary amino acids that could be generated from all the possible condons reading 3'-5' and 5'-3' for the selected amino acid. From this list, select the amino acid that occurs most frequently. For example, for valine there are 4 codons which can be read in both directions to generate a set of possible complements to valine.

| | | Valine | |
|---|---|---|---|
| Codon | Complement | 5' Translation | 3' Translation |
| GUU | CAA | ASN | GLN |
| GUC | CAG | ASP | GLN |
| GUG | CAC | HIS | HIS |
| GUA | CAU | TYR | HIS |

From this list, HIS is selected as the complement to VAL. Such selections will be referred to herein as consensus complements. The following table gives the selections for each of the amino acids.

TABLE 6A

| CONSENSUS COMPLEMENT SUBSTITUTIONS | |
|---|---|
| Amino Acid | Consensus Complement |
| ILE | TYR |
| VAL | HIS |
| LEU | GLU |
| PHE | LYS |
| MET | TYR, HIS |
| LYS | PHE |
| ASN | LEU |
| ASP | LEU |
| GLN | LEU, VAL |
| GLU | LEU |
| HIS | VAL |
| TYR | ILE |
| CYS | THR |
| ARG | ALA |
| GLY | PRO |
| TRP | THR, PRO |
| SER | SER, ARG |

TABLE 6A-continued

| CONSENSUS COMPLEMENT SUBSTITUTIONS | |
|---|---|
| Amino Acid | Consensus Complement |
| THR | CYS |
| PRO | GLY |
| ALA | ARG |

Those familiar with the production and handling of peptides will recognize that the presence of a cysteine residue in a peptide sequence may lead to problems of oxidation and dimerization in some situations. For those reasons, some investigators may wish to replace cysteine residues in complementary peptide sequences with another hydropathically neutral amino acid such as serine, and such substitutions are contemplated by this invention.

An additional preferred method to select a specific set of complementary amino acids from the general second base grouping is to determine the most frequently used (species specific) codon for each amino acid and to translate the complementary codon either 5' to 3' or 3' to 5' (referred to herein as "frequency-based complements"). Thus, for each amino acid (and each species) two frequency-based complementary amino acids may be derived and used to generate complementary peptide sequences. If a stop codon (signaling the cessation of translation in cells) is encountered in the above process. Then the second most frequently used codon for the particular amino acid can be used (and so on). Table 6B below gives the frequency-based complements for the amino acids using human codon frequencies as determined by Grantham et. al. (Nuc. Acids. Res., 9, p. r43–r75, 1981).

TABLE 6B

| HUMAN FREQUENCE BASED COMPLEMENT SUBSTITUTIONS | | |
|---|---|---|
| Amino Acid | 5'-3' Complement | 3'-5' Complement |
| ILE | ASP | TYR |
| VAL | HIS | HIS |
| LEU | GLN | ASP |
| PHE | GLN | LYS |
| MET | HIS | TYR |
| LYS | LEU | PHE |
| ASN | VAL | LEU |
| ASP | VAL | LEU |
| GLN | LEU | VAL |
| GLU | LEU | LEU |
| HIS | VAL | VAL |
| TYR | VAL | MET |
| CYS | ALA | THR |
| ARG | PRO | SER |
| GLY | ALA | PRO |
| TRP | PRO | THR |
| SER | GLY | ARG |
| THR | GLY | TRP |
| PRO | GLY | GLY |
| ALA | GLY | ARG |

Another alternative and preferred method to select a specific set of complementary amino acids from the general second base grouping is to determine the most commonly used codon for each second base group. Since codon usage frequency varies from species to species, this, approach may give different selections for different species. Using the human codon usage frequencies generated by Grantham et al. (Nuc. Acid. Res., 9, p. r43–r75, 1981), the selected simplified complementary amino acids in the following table were generated (said complementary amino acids being referred to herein as "simplified complements").

TABLE 6C

HUMAN SIMPLIFIED COMPLEMENT SUBSTITUTIONS

| Amino Acid | Simplified Complement |
|---|---|
| ILE, VAL, LEU, PHE, MET | GLU |
| LYS, ASN, ASP, GLN, GLU, HIS, TYR | LEU |
| CYS, ARG, GLY, TRP | ALA |
| SER, THR, PRO, ALA | GLY |

In some cases, a peptide may be self-complementary due to special features of its sequence. A sequence is self-complementary when it contains a point of inversion in its second base sequence. For example:

| N-terminus | Glu-Leu-Glu-Leu | Peptide sequence |
|---|---|---|
| 5' terminus | A-U-A-U | |
| 3' terminus | U-A-U-A | Complement sequence |
| C-terminus | Leu-Glu-Leu-Glu | |

Clearly, this tetrapeptide is its own complement with antiparallel orientation. This peptide has a number of other antiparallel complements with different sequences of amino acids which still have the same second base sequence. All of the antiparallel complements could be viewed as second base analogs.

The special nature of these sequences can lead to complexities of analysis of certain experimental results when a self-complementary peptide is present along with other antiparallel complements. Other antiparallel complements could have properties of conventional analogs (agonist or antagonist effects) or could have properties normally associated with complements (nonconventional antagonist and antibodies that are conventional agonists and antagonists). Regardless of the detailed mode of action of complements in these special cases, the complementary peptide principle can be used to generate new molecules with desirable, bioactive properties.

The complementary polypeptides whose sequence was determined by any of the above described methods based upon the original amino acid sequence or nucleotide codon sequence may then be obtained by chemical synthesis, directed biological synthesis or derivation (e.g. by excision) from peptides or proteins which include the determined amino acid sequences.

The complementary amino acid relationships described herin permit the design, construction and use of many polypeptide structures comprising amino acid sequences complementary to desired sequences of amino acids. The complementary amino acid sequence may be an entire peptide or polypeptide, as, for example shown herein with HTCA and gamma odne, which are respectively complementary to the entire sequence of the target peptides ACTH (1-24) or gamma-endorphin.

In particular applications, a complementary peptide may be bonded to a larger molecule by such techniques as chemical cross-linking or incorporation in a larger polypeptide structure. Complementary polypeptides may also be attached to a solid matrix for uses such as affinity chromatography.

In the practice of the present invention, particularly when a nucleotide sequence coding for a target peptide is known, it may be utilized to direct the amino acid sequence of complement. In this situation particular codons for isoleucine (AUU, AUC), leucine (UUA, CUA) threonine (ACU) or serine (UCA), may give rise to complementary codons which, when read in the 5' to 3' or 3' to 5' direction, are stop codons coding for cessation of protein synthesis. In this situation, the second base of the stop codon would be used to select an amino acid of appropriate hydropathic complementary character (from the groups shown in Tables 5 and 6). The choice from a particular group may be preferably narrowed by optimizing hydropathic complementarity. For example, with an ILE (+4.5 hydropathic score) codon (AUU or UUA) a LYS (−3.9 hydropathic score) might be chosen from the complementary second base A-group; with a serine (−0.9 hydropathic score) codon (UCA) or threonine (−0.9 hydropathic score) codon (ACU) a tryptophan (−0.9) or serine (−0.9) may be chosen from the second base G-group.

The scope of the present invention may be further described by the application of particular embodiments. For example, luteinizing hormone releasing hormone (LH-RH) is a decapeptide whose coding nucleotide sequence is unknown but has the amino acid sequence shown in the topmost line of Table 7.

TABLE 7

| | H$_2$N— | Glu— | His— | Trp— | Ser— | Tyr— | Gly— | Leu— | Arg— | Pro— | Gly— | COOH |
|---|---|---|---|---|---|---|---|---|---|---|---|---|
| LH-RH | | | | | | | | | | | | |
| Table 1 | | Leu | Val | Pro | Gly | Ile | Thr | Gln | Ala | Gly | Thr | |
| Alternatives | | Phe | Met | | Thr | Val | Ser | | Thr | Tyr | Ser | |
| | | | | | Arg | | Pro | | Ser | Pro | Pro | |
| | | | | | | | Ala | | Pro | | Ala | |
| Table 3 | | Leu | Val | Thr | Arg | Ile | Pro | Asn | Ala | Gly | Pro | |
| Alternatives | | | | | Ser | Met | | Glu | Ser | | | |
| | | | | | | | | Asp | | | | |
| Table 6 | | Ile | | Thr | Thr | Ile | Thr | Lys | Thr | Cys | Thr | |
| Alternatives | | Val | | Ser | Ser | Val | Ser | Asn | Pro | Arg | Ser | |
| | | Leu | | Pro | Pro | Leu | Pro | Asp | Ser | Gly | Pro | |
| | | Phe | | Ala | Ala | Phe | Ala | Gln | Ala | Trp | Ala | |
| | | Met | | | | Met | | Glu | | Ser | | |
| | | | | | | | | His | | | | |
| | | | | | | | | Tyr | | | | |

It is confidently predicted, based upon the knowledge and principles described herein that most, if not all, of the complements produced by the methods relating to Table 7 will display an affinity for LH-RH and prove useful in modulating the effects of this hormone.

The selection of the specific complementary peptide or peptides according to the invention having the most desirable biological or biochemical properties or effects in any given case will depend on several factors including the nature of the biological system in which the complementary peptide is to be used, whether diagnostic or therapeutic utility is desired and the type of biological effect and mode of action which is anticipated for the complementary peptide in the targeted biological system. Depending on the desired effect, some complementary peptides may be preferred over others. The following approach suggests one of many possible design schemes that can be used to generate complementary peptide sequences that will give a response in a biological, diagnostic, or physical assay at a concentration of complementary peptide of $10^{-4}$ molar or lower. This complementary peptide concentration of $10^{-4}$ molar or lower (herein referred to as the "minimum complementary peptide binding activity") is a useful parameter in selecting suitable complementary peptides according to the invention since from a practical standpoint, concentrations above that established for the minimum complementary peptide binding activity may involve impractical therapeutic dosages and lead to peptides whose binding is not specific enough to be useful in therapeutic or diagnostic applications.

The selection approach hereinafter described allows those skilled in the art to readily obtain complementary peptides which are characterized by the minimum complementary peptide binding activity. Specifically, if nucleic acid sequences are known, then four complementary peptides can be designed directly from the above disclosure (translating the complementary nucleic acid sequence either 5' to 3' or 3' to 5' and orienting the subsequent sequence of amino acids either amino-terminal to carboxy-terminal or carboxy-terminal to amino-terminal). If none of these complementary peptides has the desired level of activity or if the nucleic acid sequence of the target is not known, then two complementary peptides can be designed from an amino acid target sequence using the consensus complement approach (Table 6A) by orienting the complement amino acid sequence either amino-terminal to carboxy-terminal or carboxy-terminal to amino-terminal. If the desired level of activity has not been reached, then four additional complementary peptides can be designed using the codon usage frequency complement approach (e.g., Table 6B) by translating the species specific, most frequently used codon for each amino acid in the target sequence to its 5' to 3' complement or its 3' to 5' complement and orienting the complement amino acid sequence either amino-terminal to carboxy-terminal or carboxy-terminal to amino-terminal. Two additional complements can be designed using the simplified complement approach (e.g., Table 6C) by identifying the species specific, most frequently used amino acid for each second base grouping, generating the complementary amino acid sequence on the basis of the second base grouping of each amino acid in the target sequence, and orienting the complement amino acid sequence either amino-terminal to carboxy-terminal or carboxy-terminal to amino-terminal.

It may be observed, in a particular system, that one orientation of peptide bonds produces more desirable complementary peptides than the other, that is, peptides having the minimum complementary peptide binding activity or peptides which have a range of activities above the minimum complementary peptide binding activity. In this case, investigators may wish to limit their efforts to the more desirable orientation to simplify further experimentation. In addition, if the above design scheme has led to a particularly desirable complementary peptide, investigators may, as is commonly done, seek to find still more desirable complementary peptides by selective exchange of one or more amino acids in the complement amino acids sequence with other amino acids within the second base grouping.

The design of active or desirable complementary peptides may also be aided by the preparation of a mixture of complementary peptides, such as could be obtained in solid-phase peptide synthesis which in one or more coupling reactions several amino acid reagents could be added in one step, followed by a gradient elution of the mixture from an affinity chromatographic column containing the target peptide attached to the solid support. The most tightly bound complementary peptide will elute last. The structures of the peptides in the various elution fractions may be determined by collecting fractions and sequencing with conventional means. In this way, many peptides can be evaluated with a minimum of effort, and peptides having the minimum complementary activity can be readily obtained.

An alternative way to determine desirable complementary peptide sequences would be to generate a set of monoclonal antibodies to the target peptide, and to sequence the hypervariable regions of the gene encoding the immunoglobulin. Regions of complementarity found by sequence searching will reveal, when properly assembled, a complementary peptide sequence.

In designing complementary polypeptides, the natural amino acids may be replaced in part or in whole by analogs having a similar structure or hydropathy. For example, alanine may be replaced by alpha amino isobutyric acid, arginine by canavanine, aspartate by beta-hydroxy aspartate, leucine by norleucine, or gamma-chloroleucine, phenylalanine by beta phenylserine or D-phenylalanine, to name but a few of the many structural analogs known to those skilled in the art. The use of these replacements to construct a complementary polypeptide by a method of the present invention is deemed within the scope of the invention.

Peptides complementary to all or parts of natural hormones may be used to generate antibodies that recognize and bind the hormone receptors. These antibodies have properties of anti-idiotypic antibodies to the hormone and, thereby, may be used to purify receptors, to stimulate the biological response associated normally with the hormone, or to antagonize the effect of the natural hormone. The biological response due to antibody of a peptide complementary to a hormone is governed in part by the manner in which a particular antibody producing cell is presented with the antigen (complementary peptide). Certain presentations may be preferred, depending on the type of response desired.

Generally, peptides are coupled to carrier substrates, such as large proteins, when being used to generate antibodies. A variety of coupling technologies are known to those skilled in the art. The type of coupling used may affect the presentation of complementary peptide antigens.

Depending on the type of immunization, in vitro or in vivo, various other additives (adjuvants) may be combined with the antigen itself to moderate immune response. Such adjuvants may also affect the presentation of complementary peptide antigens.

Antibodies taken from the serum of animals are polyclonal, meaning that they are a mixture of antibodies produced by a number of sets of cells. When animals are immunized with complementary peptides, a subset of the total antibodies will bind to the complementary peptide and to the receptor of the molecule from which the complementary peptide was derived. This subset, also composed of a number of types of antibodies, can be separated from other antibodies by conventional affinity chromatography. This purified subset of antibodies is usually called mono-specific. Mono-specific antibodies to a complementary peptide may be used to purify receptors, to perform diagnostic assays for receptors, or to moderate biological response.

The mono-specific antibodies can be viewed as the set of antibodies that result from the presentation of antigen in a variety of conformations. Since the peptide antigens are somewhat flexible, they may assume many different conformations or three-dimensional structures. Each of these conformations could result in the generation of slightly different antibodies, all of which are members of the mono-specific set.

Using monoclonal techniques that are well-known in the art, it is possible to produce large amounts of a particular antibody of the mono-specific set. Such monoclonal antibodies could be screened for their ability to bind strongly to complementary peptide or receptor, to produce biological responses similar to the molecule from which the complementary peptide was derived, or to inhibit the biological response. Thus, it will be possible to select for the type of response desired.

Complementary peptides may be used in combination with adjuvants to generate vaccines. In this way, the immune system of an organism may be used to moderate the biological response of its hormone systems. The presentation of antigen may require special modifications to ensure the highest population of antibodies that give the desired biological response. Different peptides complementary to a particular bioactive peptide may yield different biological response upon vaccination due to differences in their three-dimensional conformations.

The complementary peptides of the present invention may be complementary to small peptides or portions of proteins. These complementary peptides may be utilized much as antibodies are currently often utilized. For example, a polypeptide designed according to the present invention may be prepared as complementary to a particular portion of a unique cell surface proteinaceous antigen characterizing a particular neoplasm. Such a complementary polypeptide may be chemically coupled to many materials of interest such as: a biological or chemical toxin such as ricin A chain or cisplatimum compounds; a radio-opaque substance such as a heavy metal; a radioisotope; or a fluorescent compound, to name but a few of the many possible labels or substances of interest. The polypeptide-material conjugate would specifically bind to the neoplasm and deliver a toxin or label thereto. Drug delivery systems such as Liposomes, biodegradable polymers or other encapsulating substances of interest may have specific pendant complementary polypeptides for delivery to a particular site.

Complementary polypeptides may be utilized to neutralize the activity of particular substances by binding, for example, to such as a peptide hormone, the catalytic site of an enzyme, or a peptidaceous toxin. Hormone receptors may be rendered inactive (by an antagonist) or activated (by an agonist) by administration of polypeptides complementary to a proteinaceous segment of those receptors.

Polypeptides complementary to the active sites of particular enzymes should prove to be pharmacologically effective. For example, many diabetics may benefit by administration of a polypeptide complementary to the catalytic sites of the insulin-deactivating enzymes glutathione-insulin transhydrogenase and/or the protease termed insulinase.

Many hypertensive individuals may be helped by interfering with the angiotensin system through the use of methods of this invention to design and produce peptides which are complementary to at least a portion of angiotensinogen, angiotensin I and/or angiotensin II.

In the area of endocrinology, polypeptides complementary to at least a portion of a hormone may be used to lessen or obviate hormone biological activity. For example, in Graves disease (exophthalmic goiter) a hyperfunction of the thyroid gland appears to be involved. Polypeptides complementary to thyrotropin releasing hormone (TRH) or to the beta-subunit of thyroid stimulating hormone (TSH or thyrotropin) would bind to these hormones and facilitate deactivation of the thyroid gland.

Among probable applications of the present invention is the facilitation of blood-group identification. Over 100 different blood-group antigens are present on erythrocyte surfaces to distinguish fourteen well-defined, genetically independent human blood-group systems. These antigenic groups are usually identified by erythrocyte agglutination with antibodies to specific antigens. Polypeptides complementary to specific blood-group antigens may be used instead of antibodies for blood-typing purposes. Polypeptides complementary to an amino acid sequence contained by a particular blood-group antigen may be modified to be at least divalent by crosslinking with agents such as glutaraldehyde or may be coupled to fluorescent dyes or radioisotopes. Complementary polypeptides with the former modification would agglutinate erythrocytes having the blood-group antigen targeted. The fluorescent or radioisotope modified complementary polypeptides would bind to and label erythrocytes containing the blood-group antigen targeted.

Analogously, peptides complementary to the beta chain of chorionic gonadotropin, a pregnancy specific component of biological fluids, could be utilized, by attachment of a label such as a fluorescent dye radioisotope or an enzyme yielding chromophorically measurable products, to facilitate pregnancy tests by means well established in this field.

A key to many important aspects of the immune system resides in knowledge of T cell activation by antigen binding to the T cell receptor. The T cell receptor proteins and, in 1984, the genes coding for both proteins were cloned, isolated and defined (Science V25 p859 and Science V25 p1065). By application of the methods described by the present invention, peptides complementary to different segments of the T-cell receptor may be prepared and T cell activation mechanisms systematically investigated. Allergic responses are well know to involve immunoglobulin E (IgE) mediation. Peptides complementary to segments of IgE or proteins containing peptide sequences complementary to IgE may be helpful in the alleviation of IgE mediated allergy symptoms.

The destruction of collagen, the major structural protein of the human body, during inflamation is important in the pathogenisis of a host of disease states. Activated collagenase, a hydrolytic lysosomal metalloenzyme, proteolytically attacks collagen in the initiation of pathological conditions. Polypeptides complementary to the catalytic site of collagenase should be collagenase deactivating agents. Due to the fact that mammalian collagenase hydrolyzes native type I collagen at only one particular point in each polypeptide chain, a polypeptide complementary to that same region of native type I collagen may be used to protect that collagen from collagenase-induced degradation.

Polypeptides complementary to toxic peptides or proteins serve, when properly administrered, in vivo or in vitro to bind said materials and lessen or obviate their toxicity.

Methods and compositions employing the complementary peptides of the invention, or antibodies thereto, are also afforded for the treatment of diseases associated with the overproduction or underproduction of a proteinaceous substance and for therapies wherein an increase or decrease in the biological response caused by a proteinaceous substance in beneficial. In particular, these therapeutic compositions comprise effective amounts of the complementary peptides or antibodies thereto in admixture with pharmaceutically acceptable carriers. In particular, pharmaceutical compositions that contain the complementary polypeptides of the invention, or antibodies thereto, as an active ingredient will normally be formulated with an appropriate solid or liquid carrier depending upon the particular mode of administration being used. For instance, parenteral formulations are usually injectable fluids that use pharmaceutically and physiologically acceptable fluids such as physiological saline, balanced salt solutions, or the like as a vehicle. Oral formulations, on the other hand, may be solid, e.g., tablet or capsule, or liquid solutions or suspensions.

In the therapeutic methods of the invention, the complementary polypeptides or antibodies thereto may be administered to humans or any other target organism in various manners such as orally, intravenously, intramuscularly, intraperitoneally, intranasally, intradermally, and subcutaneously. The particular mode of administration and dosage regimen will be selected by the skilled artisan taking into account the particulars of the patient, the nature of treatment required, and/or the disease and the disease state involved. For instance, infection by, or exposure to, foreign proteinaceous toxins is usually treated by daily or twice daily dosages over a few days to a few weeks; whereas a proliferative disease treatment like tumor or cancer treatment involves daily or multidaily doses over months or years. The complementary peptide or antibody therapy of the invention may be combined with other treatments and may be combined with or used in association with other chemotherapeutic or chemopreventive agents for providing therapy against those disease states or conditions against which they are effective.

A listing of such potential benefits to mankind of various applications of the present invention could proceed indefintely and include all manners of diagnostics, agent delivery, protein and cell cross-linking capabilities, neutralization of toxins from plants, bacteria or insects, and inhibition of tumor growth by numerous mechanisms including neutralization of peptide growth factors essential to certain tumor growth. The utility of the present invention extends far beyond the particular examples expressed herein.

The significance of relationships between pairing nucleotide triplet codon sequences of nucleic acids was further elucidated by studies concerning the functional activities and interrelationships of specific polypeptides. The following examples are included herein to demonstrate particular preferred embodiments of the present invention and are not meant to limit the invention unless otherwise specifically indicated by the claims herein.

EXAMPLE 1A

ADRENOCORTICOTROPIC HORMONE (ACTH, FRAGMENT CONTAINING AMINO ACIDS 1-24) AND THE DESIGN AND OBTAINING OF ITS COMPLEMENTARY POLYPEPTIDE. (HTCA, 1-24)

Synthetic ACTH, fragment 1-24 was obtained from Organon (West Orange, N.J.). The primary structure of m-RNA (messenger RNA) coding for ACTH (1-24) was obtained from Nakanishi et al (Nature (1979) Vol. 278, pp. 423–427) and is shown in Table 8. Above the m-RNA sequence the corresponding amino acid sequence for ACTH (1-24) is shown. When the m-RNA was base-paired in an antiparallel direction, the appropriate complementary nucleotide sequence (c-RNA) shown (turned parallel to the m-RNA) in Table 8 resulted. Below the c-RNA sequence is shown the amino acid sequence of HTCA, the complementary polypeptide to ACTH (1-24) resulting from reading the c-RNA sequence in the 5' to 3' direction.

TABLE 8

| ACTH, HTCA | | | | | | | | | | | |
|---|---|---|---|---|---|---|---|---|---|---|---|
| ACTH: | $H_2N$—Ser | Tyr | Ser | Met | Glu | His | Phe | Arg | Trp | Gly | Lys |
| mRNA: | 5'-UCU | UAC | UCC | AUG | GAA | CAC | UUC | CGC | UGG | GGC | AAG |
| cRNA: | 5'-GGG | GUA | CAC | CUU | CAC | CGG | GCG | CCG | CUU | CUU | GCC |
| HTCA: | a $H_2N$—Gly | Val | His | Leu | His | Arg | Ala | Pro | Leu | Leu | Ala |
| Pro | Val | Gly | Lys | Lys | Arg | Arg | Pro | Val | Lys | Val | Tyr | Pro—COOH |
| CCG | GUG | GGC | AAG | AAG | CGG | CGC | CCG | GUG | AAG | GUG | UAC | CCC-3' |
| CAC | CGG | CUU | GCC | CCA | GCG | GAA | GUG | UUC | CAU | GGA | GUA | AGA-3' |
| His | Arg | Leu | Ala | Pro | Ala | Glu | Val | Phe | His | Gly | Val | Arg—COOH |

A polypeptide having the amino acid sequence of HTCA shown above was synthesized for the inventors by Peninsula Laboratories (San Carlos Calif.)

EXAMPLE 1B

BINDING OF ACTH (1-24) TO ITS COMPLEMENTARY POLYPEPTIDE HTCA (1-24)

The methods generally described by Johnson et al (J. Immunol (1982) Vol. 129, pp. 2357–1359) were utilized to demonstrate the binding affinity of the complementary peptides ACTH and HTCA. From 1 to 25 micrograms (ug) per well of HTCA or insulin in carbonate-bicarbonate coating buffer were added to 96 well round bottom microtiter plates and incubated at 4° C. for 8 hr. The plates were then washed with phosphate buffered saline (PBS)-Tween 20 (Sigma Chemical Co., St. Louis, Mo.) buffer.

To the insulin-coated wells and to some of the HTCA-coated wells was added 10 ug synthetic ACTH (1-24) in PBS-Tween buffer. Control wells (HTCA alone) contained only PBS-Tween. The plates were incubated at room temperature for 2 hr. and then washed three times with PBS-Tween buffer. Rabbit antisera directed against the amide of synthetic ACTH 1-13 (Accurate Biochemicals, Westbury N.Y.) was added to each well and the plates were incubated for 1 hr at room temperature. Following 3 washes with PBS-Tween buffer, alkaline phosphatase-conjugated goat anti-rabbit Ig G (Miles Laboratories, Elkharbt, Ind.) in PBS-Tween buffer (1:300 dilution) was added. After inculation at room temperature for 1 hr, the plates were washed three times with PBS-Tween buffer and each well was treated with 200 microliters (ul) of p-nitrophenyl phosphate (1 mg/ml in carbonate-bicarbonate buffer) for 1½ hr. at room temperature. The enzymatic reaction was then stopped by the addition of 3N NaOH (50 ul) to each well and the optical absorbance of p-nitrophenol the alkaline phosphatase product, was measured at 405 nm. The ACTH bound to the coated microtiter wells was measured by this enzyme-linked immunoabsorbent assay (ELISA).

Figure 3:
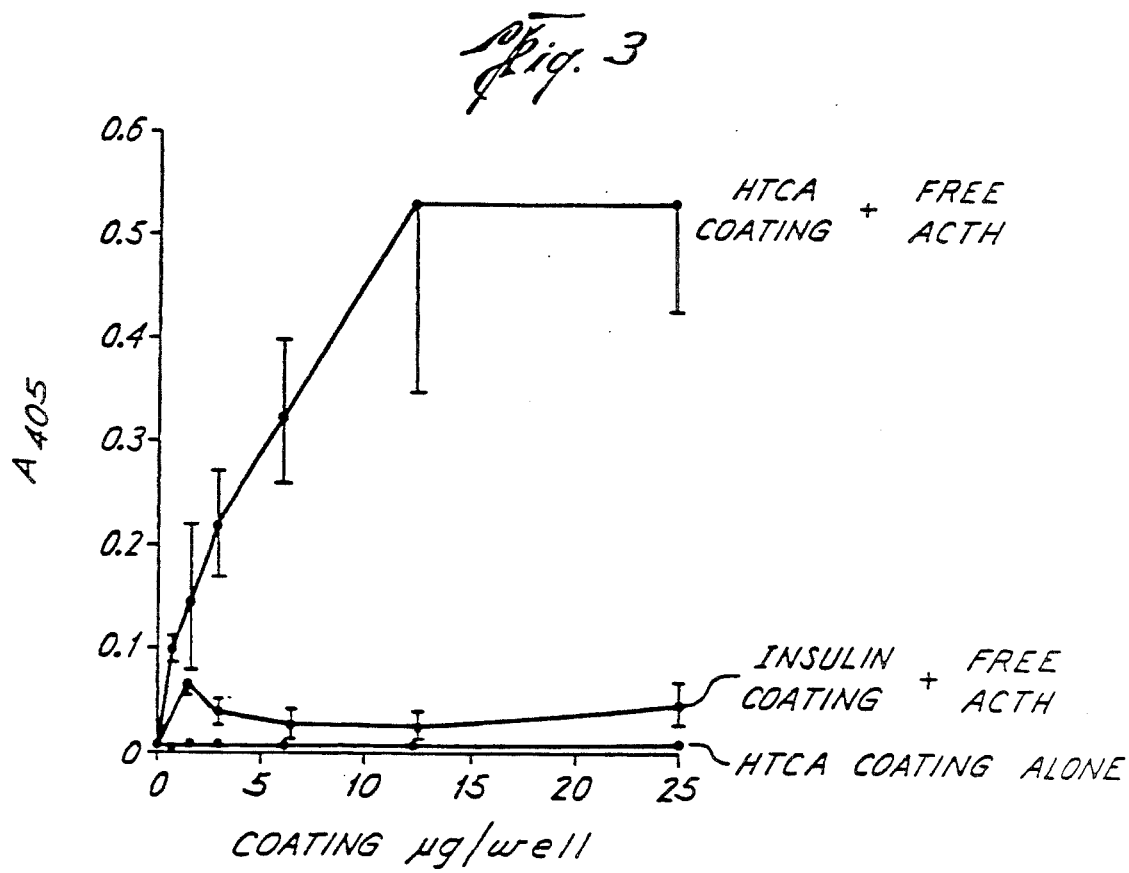
FIG. 3 graphically depicts the binding of free ACTH to microtiter wells coated with HTCA (a complementary peptide to ACTH) or insulin. Bound ACTH was measured by an enzyme-linked immunoabsorbent assay.

The results of this experiment are shown in FIG. 3. Synthetic ACTH (1-24) is bound by HTCA coated microtiter wells but not by insulin coated microtiter wells. The antibody specific for ACTH (1-13 amide) does not bind to the coating of HTCA, and nor does ACTH bind to the coating of insulin. The molar amount of ACTH bound was directly proportional to the concentration of HTCA coating which suggests a one to one binding of the two peptides (data analysis not shown).

Figure 4:
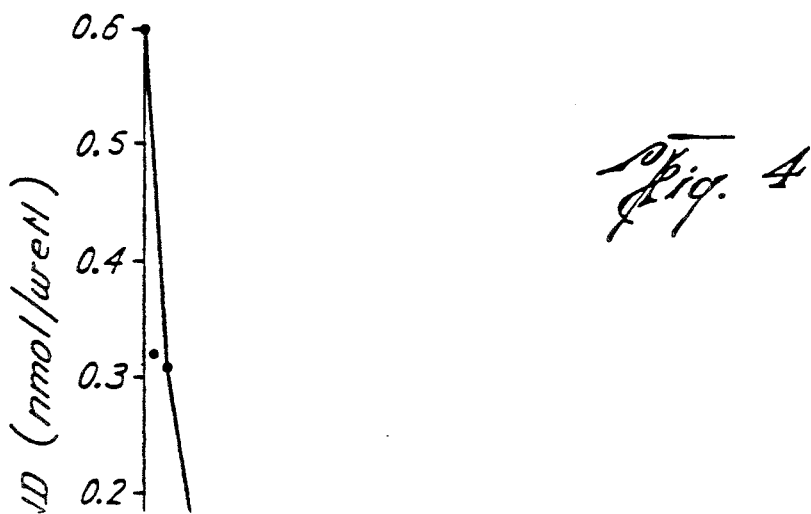
FIG. 4 graphically depicts the binding of ACTH to microtiter wells each coated with HTCA (3.7 nmol/well). Each ACTH addition contained 3.7 nmol soluble ACTH and was premixed with the amounts of soluble HTCA designated on the abscissa. Bound ACTH was measured by enzyme-linked immunoabsorbent assay and free ACTH calculated by the difference between total ACTH and bound ACTH.

A microtiter plate was prepared and treated generally as described above but was coated with 3.7 nmol/well HTCA. To each coated well was added a solution of 3.7 nmol ACTH combined with the amounts of HTCA designated on the abscissa in FIG. 4. When ACTH binding was evaluated by an ELISA, it showed that about 90% of ACTH-HTCA binding was specific. A Scatchard analysis (not shown) of the data from FIG. 4 showed a single uniform binding site with a Kd of 1.9 micromolar, comparable to the affinity shown by an antibody-antigen complex.

EXAMPLE 1C

Binding of $I^{125}$ ACTH TO 3'-5' HTCA

Utilizing the complementary RNA (cRNA) sequence shown in Table 8 of Example 1A, but reading the cRNA in the 3' to 5' direction, the following amino acid sequence was obtained and the respective peptide (3'-5' HTCA) chemically synthesized:

H$_2$N—Arg—Met—Arg—Tyr—Leu—Val—Lys—Ala—Thr—Pro—Phe—Gly—His—Pro—Phe—Phe—Ala—Ala—Gly—His—Phe—His—Met—Gly—COOH.

Utilizing techniques described in Example 1B, polyvinyl microtiter wells were coated with 3'-5' HTCA from a 1 mM solution thereof or with BSA.

The BSA and 3'-5' HTCA coated wells were washed and then treated with one of three solutions of $I^{125}$ ACTH (1-39) (New England Nuclear Boston, MA) having different concentrations. After a forty five minute incubation period the solution was removed and the microtiter wells extensively washed. The microtiter wells were separated and assayed for iodine$^{125}$ content in a Beckman Gamma 5500 gamma counter. The results of these manipulations are shown in Table 9. Bound $^{125}$I-ACTH was measured in duplicate at three concentrations in the absence and presence of excess unlabelled ACTH.

TABLE 9

| | ACTH and 3'-5' HTCA | | |
|---|---|---|---|
| | Bound CPM - $^{125}$I-ACTH | | |
| | BSA Coating | 3'-5' HTCA Coating | + Excess ACTH |
| conc $^{125}$I-ACTH | 159 | 1819 | 616 |
| | 160 | 1716 | 615 |
| 1:3 dilution $^{125}$I-ACTH | 155 | 601 | 287 |
| | 165 | 590 | 299 |
| 1:9 dilution $^{125}$I-ACTH | 133 | 263 | 191 |
| | 114 | 289 | 183 |

As shown by the data in Table 9, $^{125}$I-ACTH binds to coated 3'-5' HTCA but not to coated BSA, a well-known protein with a wide binding capacity. The binding of $^{125}$I-ACTH to 3'-5' HTCA-coated microtiter wells is inhibited by the presence of excess free ACTH. This result demonstrates both the affinity of a complementary peptide to an original peptide and the fact that such complementary polypeptides may be designed and obtained by reading the sequence of complementary nucleic acid codons in the 3' to 5' direction and chemically synthesizing the peptide so directed.

EXAMPLE 1D

BINDING OF $^{125}$I-ACTH TO COMPONENT PEPTIDE SEQUENCES OF HTCA

Utilizing the cRNA sequence and HTCA sequence shown in Table 8 of Example 1A, a series of peptides having a carboxy-terminal portion of the HTCA amino acid were synthesized. A pentamer (5-mer) contained the amino acid sequence: H$_2$N-Phe-His-Gly-Val-Arg-COOH. A decamer (10-mer) contained the amino acid sequence: H$_2$N-Ala-Pro-Ala-Glu-Val-Phe-His-Gly-Val-Arg-COOH. A twenty membered peptide (20-mer) contained the amino acids sequence: H$_2$N-His-Arg-Ala-Pro-Leu-Leu-Ala-His-Arg-Leu-Ala-Pro-Ala-Glu-Val-Phe-His-Gly-Val-Arg-COOH. Each of thes peptides was used to coat microtiter wells and the coated wells tested for the ability to bind $^{125}$I-ACTH as described in Example 1C. The results of these manipulations are shown in Table 10.

TABLE 10

| | $^{125}$I-ACTH Binding to HTCA Components | | | | | | |
|---|---|---|---|---|---|---|---|
| | CPM bound $^{125}$I-ACTH | | | | | | |
| | BSA Coating | 5-mer Coating | + excess ACTH | 10-mer Coating | + excess ACTH | 20-mer Coating | + excess ACTH |
| conc $^{125}$I-ATCH | 159 | 10,252 | 233 | 8,927 | 345 | 1978 | 229 |
| | 160 | 11,388 | 245 | 9,072 | 350 | 1768 | 213 |
| 1:3 dilution $^{125}$I-ATCH | 155 | 3,514 | 97 | 3391 | 132 | 613 | 113 |
| | 165 | 3,655 | 95 | 2931 | 143 | 625 | 83 |
| 1:9 dilution $^{125}$I-ATCH | 133 | 995 | 56 | 872 | 62 | 238 | 39 |
| | 114 | 993 | 52 | 1062 | 58 | 215 | 48 |

As shown by the data in Table 10, the peptides from the HTCA sequence all exhibit the ability of binding $^{125}$I-ACTH.

EXAMPLE 1E

HTCA with Reversed Directionality and Binding of $^{125}$I-ACTH (1-39) thereto A 24-mer HTCA variant (R-HTCA) with reversed amino acid sequence directionality (amino-terminal and carboxy-terminal ends being reversed) was synthesized and had the following sequence: H₂N-Arg-Val-Gly-His-Phe-Val-Glu-Ala-Pro-Ala-Leu-Arg-His-Ala-Leu-Leu-Pro-Ala-Arg-His-Leu-His-Val-Gly-COOH. The well-coating and $^{125}$I-ACTH binding procedures were performed as described in Example 1-C and the resultant data shown in Table 11.

TABLE 11

$^{125}$I-ATCH Binding to R-HTCA
CPM Bound $^{125}$I-ATCH

| | BSA | R-HTCA | + Excess ACTH |
|---|---|---|---|
| conc $^{125}$I-ATCH | 159 | 10,392 | 303 |
| | 160 | 10,709 | 325 |
| 1:3 dil. $^{125}$I-ATCH | 155 | 2,997 | 140 |
| | 165 | 3,209 | 121 |
| 1:9 dil. $^{125}$I-ATCH | 133 | 1,101 | 65 |
| | 114 | 1,161 | 69 |

As demonstrated in Table 11, the R-HTCA polypeptide, complementary to ACTH, has a significant affinity for ACTH. This exhibits yet another aspect of the present invention, the reversed directionality specifically tested here permits a further variance in the design of polypeptides where an optimal set of chemical, physical and biological effects may be sought for a particular circumstance or application. If HTCA is understood as having an amino acid sequence antiparallel to the ACTH sequence, then the R-HTCA sequence is parallel to the ACTH amino acid sequence. Thus both parallel and antiparallel peptides or polypeptides complementary to an original or target amino acid sequence effectively have affinities therefor. The complementarity or affinity of a complementary polypeptide to an original peptide or protein is retained, regardless of the amino-terminal and carboxy-terminal directionality of said complementary polypeptide.

EXAMPLE 1F

PREPARATION AND PROPERTIES OF ANTIBODY TO HTCA.

An antigenic form of HTCA was prepared by coupling 200 ug HTCA to 200 ug keyhole limpet hemocyanin (KLH) with 6.7 mM glutaraldehyde according to the methods of Avrameas et al (Immunochemistry (1969) Vol. 6, pp. 53–66). Excess glutaraldehyde was removed from the HTCA-KLH conjugate by passage through a Bio-Rad P-10 column (Bio-Rad, Richmond, CA).

Three injections, containing 25 ug, HTCA-KLH in 0.5 ml complete Freunds adjuvant were administered to a rabbit at two-week intervals. Total immunoglobulin from the resulting rabbit antiserum was isolated by immunoaffinity chromatography on a column of Sepharose 4B (Pharmacia Fine Chemicals, Uppsala, Sweden,) coupled to goat anti-rabbit immunoglobulin. To purify the anti-HTCA antibody, KLH antibody was removed from the total immunoglobulin by passage through a column of Sepharose 4B coupled to KLH. A 1:300 dilution of the purified antibody preparation (anti-HTCA) would detect at least 100 ng of the HTCA in an indirect ELISA.

An induction of glucocorticoid hormone production by ACTH and anti-HTCA was found with cultured mammalian cells. Duplicate cultures of mouse adrenal tumor (Y-1) cells in microtiter plates were treated with culture media, ACTH (10 microunits/well) or various dilutions of the anti-HTCA. The results of this experiment are shown in Table 12.

TABLE 12

| Addition[a] | Corticosterone equivalents (ug/ml)[b] | |
|---|---|---|
| | Experiment 1 | Experiment 2 |
| ACTH | 1.08 | 1.42 |
| anti-HTCA 1:3 | 1.19 | 1.03 |
| 1:19 | N.D. | 0.78 |
| 1:30 | N.D.[c] | 0.62 |
| Media | 0.66 | 0.68 |

[a]Duplicate cultures of mouse adrenal (Y-1) cells in microtiter plates were treated with culture media, ACTH (10 microunits/well) or the indicated dilutions of antibody to HTCA. After 18 hrs incubation at 37° in 4% CO₂, replicate cultures were pooled and assayed for glucocorticoid hormone production by a radioimmunoassay (RIA) for corticosterone (Smith et al, Science (1982), Vol. 218, pp. 1311-1312)
[b]Parallel dose reponses for experimental samples and the corticosterone standard were obtained over a ten fold range. Interassay variation was 8.8 percent.
[c]Not done.

The activation of the mouse adrenal tumor cell ACTH receptor by anti-HTCA indicates a configurational analogy of the antibody and ACTH. Neither normal rabbit serum nor antibody to KLH caused a steroidogenic response (data not shown). The activation of receptors for insulin (Sege et al, Proc. Nat'l. Aca. Sci. (1978) and for beta-adrenergic agents (Schreiber et al, Proc. Nat'l. Acad. Sci. (1980), Vol. 77, pp. 7385–7389) by anti-idiotypic antibodies raised against antibodies for insulin or beta adrenergic agents has been described. Thus, a relationship of analogy exists between to complementary peptide ligands and anti-idiotypic antibodies.

EXAMPLE 1G

BINDING OF ANTI-HTCA TO MOUSE ADRENAL TUMOR (Y-1) CELLS

Figure 5:
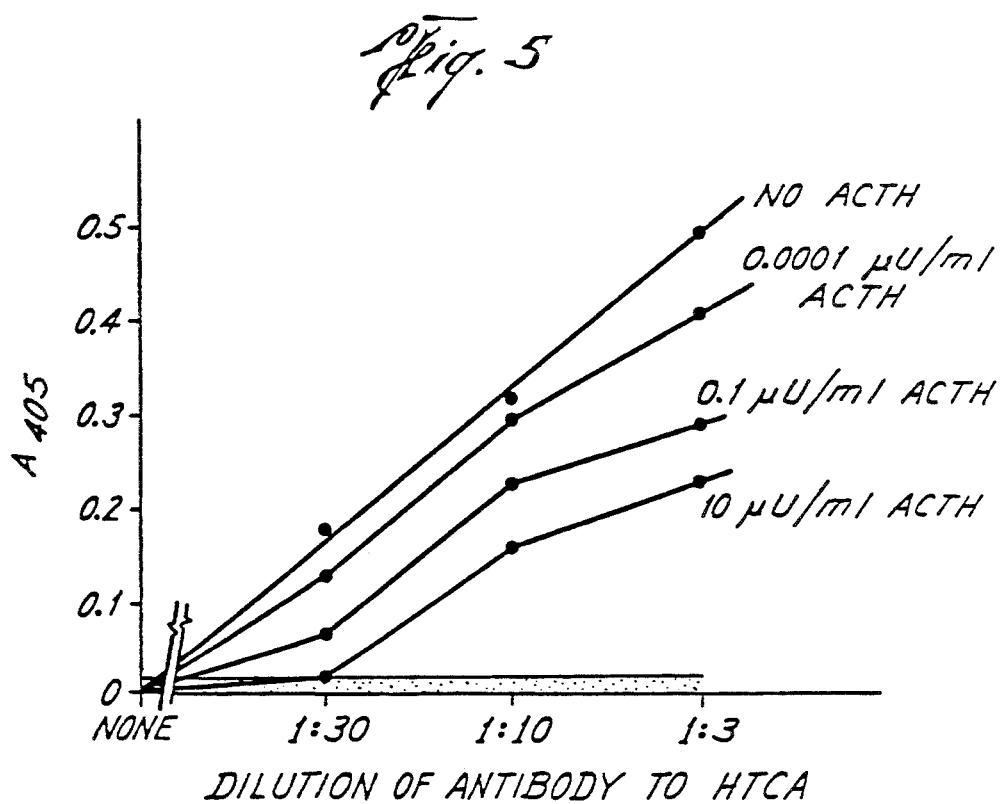
FIG. 5 graphically depicts the binding of antibody for HTCA (anti-HTCA) to affixed mouse adrenal (Y-1) cells and the inhibition of this binding by ACTH.

Mouse adrenal tumor (Y-1) cells were affixed by glutaraldehyde in flat bottom wells of a microtiter plate. The affixed cells were then treated with rabbit anti-KLH or rabbit anti-HTCA alone or in the presence of several levels of ACTH. After washing, the microtiter wells were treated with goat antibody to rabbit immunoglobulin the goat antibody being coupled to the enzyme alkaline phosphatase. After washing away unbound antibody-phosphatase complex, p-nitrophenyl phosphate was added and the enzyme dependent development of absorbancy at 405 nM was monitored. As shown in FIG. 5, ACTH blocked binding of the anti-HTCA in a dose dependent manner. ACTH and anti-HTCA appeared competitive for the same binding site on the mouse adrenal tumor (Y-1) cells. Rabbit anti KLH had no effect (shaded region).

EXAMPLE 1H

PURIFICATION OF ACTH RECEPTOR

Purified anti-HTCA was covalently coupled to cyanogen bromide-activated Sepharose 4B. Approximately 10⁸ mouse adrenal tumor (Y-1) cells were sonicated for 5 min. at 40 KHZ (Branson E Module Bath Sonicator) in the presence of 2 mM phenylmethylsulfonyl fluoride.

Figure 6:
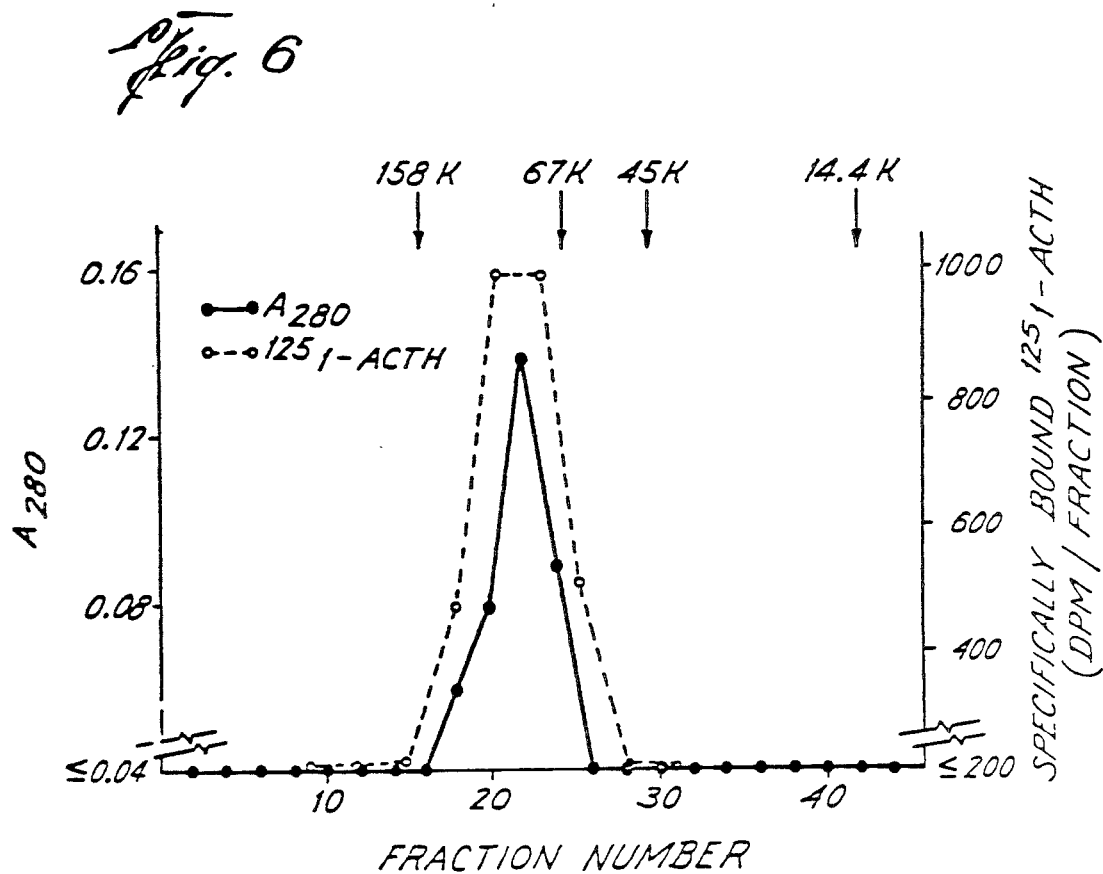
FIG. 6 graphically depicts the eluent from gel chromatography of mouse adrenal (Y-1) cell components which had previously bound to anti-HTCA.

After removal of cell debris by centrifugation, the supernatant fluid was passed through a chromatographic column containing Sepharose 4B coupled to anti HTCA. After extensive washing, the residual binding material was eluted from the column with 0.1M glycine, pH 2.0. The eluted material was neutralized and concentrated by dialysis against dry polyethylene glycol. The concentrated material was then subjected to gel chromatography on a calibrated column of Sephacryl S-200 (Pharmacia, Fine Chemicals, Uppsala, Sweden). Aliquots of the gel chromatography fractions were assayed for ACTH receptor activity by a radio receptor procedure. Briefly, this procedure involved incubation of the above aliquots in 96-well polyvinyl plates for 18 hr, followed by removal of unbound materials by washing. Radioiodinated ACTH ($^{125}$I-ACTH, 70 microcuries/ug, New England Nuclear, Boston, MA) was then added to the wells in the presence or absence of an unlabeled ACTH excess (10 ug/well). The plates were then extensively washed and the wells were excised from the plate and measured for $^{125}$I-ACTH with a Beckman Gamma 5500 gamma counter. The chromatographic fractions were also monitored for absorbance at 280 nM. The results of this Example are shown in FIG. 6.

Specifically bound $^{125}$I-ACTH was found by subtracting the radioactivity bound in the presence of excess unlabeled ACTH (generally less than 10%) from radioactivity bound in the absence of unlabeled ACTH. The elution points for the 158 kilodalton (K), 67K, 45K and 14.4K molecular weight standards are indicated by the arrows.

The ACTH receptor activity had a molecular weight of about 80 to 100K, which was similar to that previously reported for an ACTH receptor identified by a photoaffinity labeling technique (Ramachandran et al, Proc. Nat'l. Acad. Sci. (1980), Vol. 77, pp. 3697-3970).

The procedure described in this example demonstrates a general method of the invention for obtaining components of any peptide or protein ligand receptor site. A polypeptide complementary to at least a portion of the peptide or protein is first provided. An antibody against said complementary polypeptide is then prepared. The antibody is then coupled by chemical or adsorptive means to a solid matrix. A receptor-containing sample is then treated with the antibody-coupled matrix to specifically bind components of the receptor site. Finally the bound components are eluted.

EXAMPLE 1I

GAMMA ENDORPHIN, THE DESIGN AND OBTAINING OF ITS COMPLEMENTARY POLYPEPTIDE

To further illustrate the general applicability and significance of the present invention, a second pair of interactive complementary peptides was studied. Positions 104 to 120 of the amino acid sequence of bovine gamma endorphin precursor and mRNA sequence coding therefor were shown by Nakanishi et al (Nature (1979), Vol. 278, pp. 423-427). Table 13 shows this gamma endorphin amino acid sequence (designated endo) and corresponding m-RNA sequence. The complementary strand of RNA (c-RNA) base-pairing in an antiparallel direction with the m-RNA for gamma-endo is shown beneath the m-RNA, the cRNA is shown in Table 5 parallel to the m-RNA. The polypeptide (gamma-odne) whose sequence is directed by reading the c-RNA in the 5' to 3' direction is shown beneath the c-RNA (designated gamma-odne).

TABLE 13

| -endo: | H$_2$N—tyr—gly—gly—phe—met—thr—ser—glu |
| --- | --- |
| m-RNA: | 5'-UAC—GGC—GGG—UUC—AUG—ACC—UCC—GAG |
| cRNA: | 5'-CAG—CGU—GAC—AAG—GGG—CGU—UUG—GCU |
| -odne: | H$_2$N—gln—arg—asp—lys—gly—arg—leu—ala |

| | lys—ser—gln—thr—pro—leu—val—thr—leu—COOH |
| --- | --- |
| | AAG—AGC—CAA—ACG—CCC—CUU—GUC—ACG—CUG3' |
| | CUU—CUC—GGA—GGU—CAU—GAA—CCC—GCC—GUA3' |
| | leu—leu—gly—gly—his—glu—pro—ala—val—COOH |

A polypeptide having the amino acid sequence of gamma-odne was synthesized for the inventors by Peninsula Laboratories (San Carlos, CA).

EXAMPLE 1J

PROPERTIES OF GAMMA ( )-ODNE, THE POLYPEPTIDE COMPLEMENTARY TO GAMMA-ENDORPHIN ( -ENDO)

Synthetic bovine gamma-endorphin was obtained from Boehringer Mannheim (Indianapolis, IN) and rabbit antibody for synthetic gamma-endo was obtained from Accurate Biochemicals (Westbury, NY).

Figure 7:
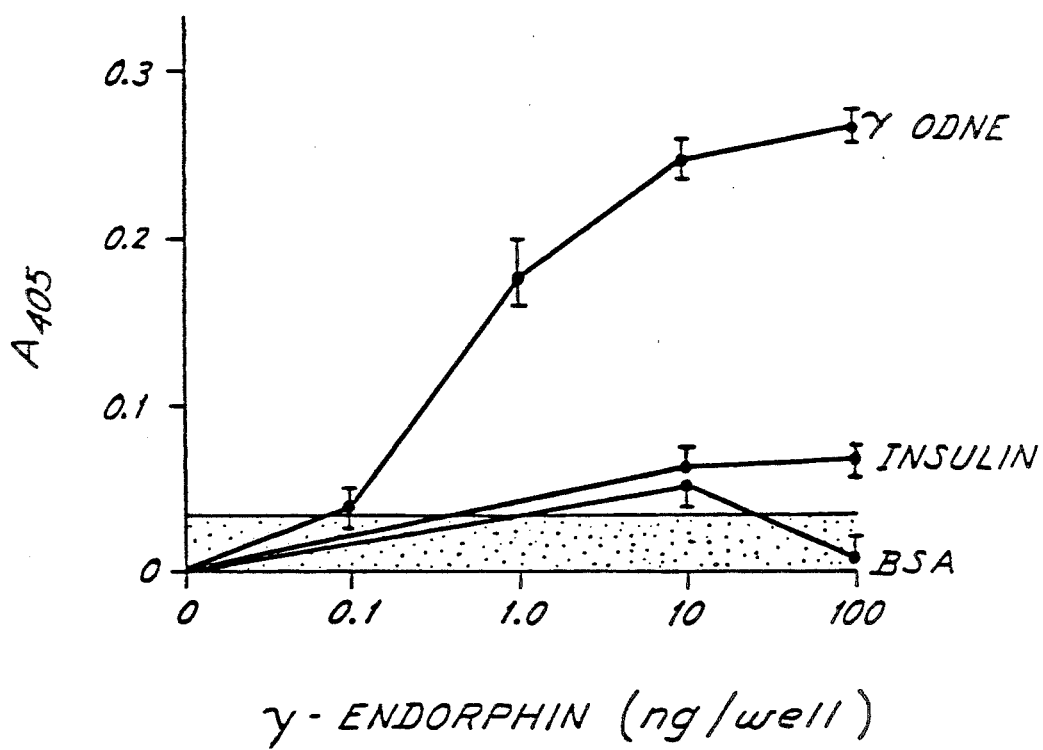
FIG. 7 graphically depicts the binding of gamma () -endorphin from various amounts added to microtiter wells coated with: a peptide (gamma-odne) coded by the nucleotide strand complementary for bovine gamma endorphin, 40 ug/well; insulin, 20 units/well; or bovine serum albumin (BSA), 200 ug/well.

The wells of a 96-well round-bottomed microtiter plate were coated (by the procedure described in Example 1B) with gamma-odne (40 ug/well), insulin (20U/well) or bovine serum albumin (BSA, 200 ug/well). Varying concentrations of gamma-endorphin (as shown on the abscissa in FIG. 7) were incubated in the coated wells for 1 hr, after which the plates were thrice washed with PBS-Tween buffer. The wells were then treated with rabbit antibody for gamma-endorphin, washed, and then treated with goat antibody against rabbit immunoglobulin the goat antibody being conjugated to alkaline phosphatase. After washing away unbound goat antibody conjugate, the bound alkaline phosphatase activity was measured with p-nitrophenylphosphate as earlier described. The results of the above manipulations are shown in FIG. 7 where the extent of absorbance at 405 nM reflects the degree of gamma-endorphin binding to wells coated with gamma-odne, insulin or BSA. It was clear that gamma-endorphin significantly bound to the affixed gamma-odne as compared to its binding to affixed insulin or BSA. The shaded area in FIG. 7 represents the extent of gamma-endorphin binding in the presence of soluble excess of gamma-odne. Thus it is shown that a second pair of complementary peptides interacts in a manner showing affinity and apparent congruence.

EXAMPLE 1K

GENERAL APPLICABILITY FOR PRODUCTION OF COMPLEMENTARY POLYPEPTIDES

The results of Examples 1A through 1J demonstrate particular applications of a general method for designing and obtaining polypeptides complementary for proteins or peptides having on at least partially known nucleotide coding sequence. For example, the complementary nucleotide sequence which codes for a polypeptide complementary to at least a portion of a first protein or peptide when read in a 5' to 3' direction may be DNA. Said DNA may be inserted into a plasmid to form a recombinant DNA transfer vector. A unicellular organism, suitably a bacteria yeast or mammalian cell may then be transformed with the recombinant DNA vector to produce a transformant unicellular organism biosynthesizing said complementary polypeptide. The techniques for such insertions and transformations are well known in the relevant fields.

Techniques of chemical polypeptide synthesis from amino acids, as well as methods of obtaining polypeptides for example by a proteolytic excision from proteins having of a larger amino acid sequence but containing the complementary amino acid sequence desired are also known. Thus, many ways of obtaining polypeptides complementary to peptide or protein ligand are available.

EXAMPLE 1L

Blocking of stress response in mice by a peptide complementary to Adrenocorticotropic Hormone (ACTH)

In response to various stresses, animals produce adrenocorticotropic hormone (ACTH), which acts on adrenal cells to produce elevated serum levels of corticosterone. To test the effectiveness of the inhibition of activity of ACTH in vivo by a complementary peptide, HTCA (see Example 1A). the following sets of experiments were performed. Mice (BALC/c) were injected with the complementary peptide HTCA, held for a period of time, stressed, decapitated, and serum corticosterone levels were determined by conventional immunoassay.

In the first experiment, 1 mg HTCA dissolved in PBS (phosphate buffered saline) was injected into 8 sets of 3 BALB/c mice each. Two sets of 3 BALB/c mice were injected only with PBS. The mean corticosterone levels of each set of mice was determined after various delay and stress regimens. The results are presented in Table 14, where the stress is a 30 second immersion in ice water.

TABLE 14

| Injection | Route* | Delay (hr) | Stress | Corticosterone (ug/dl) |
|---|---|---|---|---|
| PBS | IM | 0 | none | 18 |
| PBS | IM | 0 | YES | 75 |
| HTCA | IM | 0.5 | YES | 90 |
| HTCA | IM | 1.0 | YES | 55 |
| HTCA | IM | 2.0 | YES | 40 |
| HTCA | IM | 4.0 | YES | 60 |
| HTCA | IP | 0.5 | YES | 95 |
| HTCA | IP | 1.0 | YES | 85 |
| HTCA | IP | 2.0 | YES | 75 |
| HTCA | IP | 4.0 | YES | 65 |

*IM - intramuscular injection
IP - intraperitoneal injection

The maximum effect observed, about a 50% reduction in serum corticosterone, occured with stress occuring 2 hours after intramuscular injection of 1 mg of HTCA. In a second experiment, various amounts of HTCA were injected (IM) into sets of 3 BALB/c mice. Mice were held for 2 hours and stressed with immersion in ice water. Table 15 shows the mean serum corticosterone levels for the various sets of mice.

TABLE 15

| Injection | Stress | Corticosterone (ug/dl) |
|---|---|---|
| PBS | NONE | 8 |
| PBS | YES | 42 |
| 0.01 mg HTCA | YES | 44 |
| 0.1 mg HTCA | YES | 37 |
| 1.0 mg HTCA | YES | 30 |

Combined, these experiments show the ability of a peptide complementary to ACTH to lower the corticosterone stress response in mice.

EXAMPLE 1M

Blocking of Binding of $^{125}$I-beta-endorphin to NG108-15 cells by a peptide complementary to gamma-endorphin NG108-15 cells are known to contain receptors for beta-endorphin called opiate receptors. In addition to beta-endorphin, gamma-endorphin and several analogs of beta-endorphin bind to these opiate receptors. The peptide, gamma-ODNE, complementary to gamma-endorphin described in Example 1I was examined for its ability to inhibit the binding of $^{125}$I-beta-endorphin to opiate receptors on NG108-15 cells. Gamma-endorphin is a fragment of the larger peptide beta-endorphin.

In separate experiments, the specific binding of $^{125}$I-beta-endorphin to NG108-15 cells plated in microtiter wells was determined by competition with unlabelled beta-endorphin. Seventy percent of the total binding was specific by conventional criteria.

For this experiment, $^{125}$I-beta-endorphin was preincubated 30 minutes with various amounts of the complementary peptide, gamma-ODNE, before a 30 minute (37° C.) incubation with NG108-15 cells in microtiter wells. After the incubation, cells were washed 3 times and cell associated radioactivity wad determined with a Packard Multi-Prias gamma counter. Table 16 demonstrates the ability of gamma-ODNE to inhibit the binding of $^{125}$I-beta-endorphin ($10^{-11}$M, 2000 Cl-mmol) to NG108-15 cells.

TABLE 16

| Gamma-ODNE Concentration | % Inhibition of Specific $^{125}$I-beta-endorphin |
|---|---|
| $10^{-6}$M | 24.7 ± 3.9 |
| $10^{-5}$M | 36.0 ± 2.1 |
| $10^{-4}$M | 75.0 ± 0.6 |

EXAMPLE 1N

Induction of catatonia in mice by antibodies to a peptide complementary to gamma-endorphin It is well known that large doses of opiate-like substances can induce a catatonic state in animals which is inhibited or reversed by treatment with the opiate antagonist naloxone. In analogy with the results in earlier examples, the ability of a peptide (gamma-ODNE) complementary to an opiate peptide, gamma-endorphin, to induce antibodies that have opiate properties was examined.

Gamma-ODNE (Example 1I) was conjugated to Keyhole Limpet Hemocyanin (KLN) and used with Freund's adjuvant to generate rabbit antibodies in a conventional manner (see Example 1F). Both normal and induced rabbit sera were injected intracerebroventicularly (i.c.) into female ICR mice. Injection of 50 ul of normal rabbit serum (diluted 1:100) resulted in no induction of opiate-like catatonia. Injection of 50 ul of complementary peptide (gamma-ODNE) induced rabbit serum (diluted 1:100) resulted in an excellent induction of catatonia, which was reversed by the simultaneous i.c. injection 0.2 mg of the opiate antagonist naloxone.

These results demonstrate the ability of an antibody to a complementary peptide to an opiate to itself show opiate activity.

EXAMPLE 10

Antigenic Relationship Between Two Peptides Complementary to Adrenocorticotropic Hormone (ACTH)

Two peptides complementary to ACTH, described in Examples 1B and 1C as HTCA and 3'-5' HTCA, were each coupled to Keyhole Limpet Hemocyanin (KLH) with glutaraldeyde (1 mg peptide, 1 mg KLH, 30 mM glutaraldehyde for 30 minutes at room temperature followed by dialysis) to prepare antigens for rabbit immunization. Two rabbits were injected separately with 250 ug of peptide-KLH antigens weekly for four weeks. Each rabbit was bled biweekly for three weeks following the last injection. Antibodies representing the total immunoglobulin from serum of each rabbit was purified by precipitation from serum with 50% saturated ammonium sulfate at 4° C. followed by standard ion exchange chromatography on a DEAE column.

To examine the binding of each of the immunoglobulins to each of the peptides, enzyme-linked immunosorbant assays were performed. In these assays, one of the complementary peptides was coated onto polycarbonate plates in a carbonate coating buffer at pH 9.0 overnight. Unbound peptide was removed by washing three times with phosphate buffered saline (PBS)-TWEEN 20. Various amounts of immunoglobulins were added to peptide-coated wells in PBS-TWEEN 20 solution and incubated for one hour. Unbound immunoglobulin was removed by washing with PBS-TWEEN 20. To each well was added a 1:300 dilution of goat anti-rabbit IgG coupled to alkaline phosphatase enzyme. After one hour the wells were washed with PBS-TWEEN 20 to remove unbound secondary antibodies. The amount of remaining secondary antibody was determined by reacting p-nitrophenyl phosphate with the remaining aklaline phosphatase enzyme for 15 minutes, stopping the reaction with 3M NaOH, and measuring nitrophenol produced spectrophotometrically at 490 nm.

Table 17 gives the results of the assay. Not shown are three controls (ACTH plates+immunized rabbit immunoglobulin, HTCA plates+normal rabbit immunoglobulin, and 3'-5' HTCA plates+normal rabbit immunoglobulin) all of which showed less than 0.01 absorbance in the assay.

TABLE 17

| Antibody Added mg/ml | Immunogen | Absorbance at 490 nm |
|---|---|---|
| Plates coated with HTCA | | |
| 0.012 | 3'-5' HTCA | 0.08 ± 0.04 |
| 0.04 | 3'-5' HTCA | 0.24 ± 0.08 |
| 0.11 | 3'-5' HTCA | 0.37 ± 0.09 |
| 0.3 | 3'-5' HTCA | 0.91 ± 0.11 |
| 0.11 | HTCA | 0.98 ± 0.18 |
| Plates coated with 3'-5' HTCA | | |

TABLE 17-continued

| Antibody Added mg/ml | Immunogen | Absorbance at 490 nm |
|---|---|---|
| 0.012 | HTCA | 0.05 ± 0.01 |
| 0.04 | HTCA | 0.12 ± 0.06 |
| 0.11 | HTCA | 0.44 ± 0.06 |
| 0.3 | HTCA | 1.39 ± 0.21 |
| 0.11 | 3'-5' HTCA | 0.89 ± 0.23 |

These results demonstrate that antibodies to one complementary peptide recognize and bind to another complementary peptide. Thus, the two complementary peptides are antigenically related even though their sequences have only one position where the same amino acid occurred in the same absolute position.

EXAMPLE 1P

Idiotype:Anti-idiotype Relationship between Antibodies to Adrenocorticotropic Hormone (ACTH) and Antibodies to a Peptide Complementary to ACTH Using a standard Radioimmunoassay (RIA) for ACTH (Immuno Nuclear Corporation, CAT. #2400), the ability of antibodies to a peptide (HTCA) complementary to ACTH to bind with antibodies to ACTH was determined. In a Standard RIA for ACTH, unlabelled ACTH is added in known amounts to a solution of radiolabelled ACTH and antibody to ACTH to compete away the binding of radiolabelled ACTH to its antibody. The amount of radiolabel bound is determined by immunoprecipitating the antibody and counting the radioactivity of the precipitiate.

In the experiment, unlabelled ACTH, immunoglobulin from rabbits immunized with the complementary peptide HTCA, and immunoglobulins from normal rabbits were used to compete with radiolabelled ACTH in the RIA. Immunoglobulin (35 mg/ml) solutions were prepared in phosphate buffered saline, and ACTH and $^{125}$I-ACTH were prepared as specified in the RIA kit. Table 18 gives the results of the competion assay.

TABLE 18

| Competitor Added | Percent Specific Binding |
|---|---|
| none | 100 |
| 20 pg/ml ACTH | 90 |
| 50 pg/ml ACTH | 77.5 |
| 100 pg/ml ACTH | 62.2 |
| 200 pg/ml ACTH | 42 |
| 500 pg/ml ACTH | 21.6 |
| IgG HTCA (1:10 dilution) | 0 |
| IgG HTCA (1:30 dilution) | 10 |
| IgG HTCA (1:100 dilution) | 26.3 |
| IgG HTCA (1:300 dilution) | 73.6 |
| IgG HTCA (1:1000 dilution) | 100 |
| Normal (1:100 dilution) | 89.3 |
| Normal (1:1000 dilution) | 94.4 |

These results demonstrate that antibodies to a peptide complementary to ACTH recognize and bind to antibodies to ACTH and thus define an idiotype:anti-idiotype relationship between the antibodies.

EXAMPLE 1Q

In Vivo Activity of Antibodies to a Peptide Complementary to Adrenocorticotropic Hormone (ACTH) Generated by Animal Vaccination A peptide complementary to ACTH (see HTCA example 1A) was conjugated to Keyhole Limpet Hemocyanin (KLH) using the procedure described in Example 10. Three BALB/c mice per time point were immunized (100 ug conjugate/0.2 ml complete Freund's adjuvant on day 0 injected intraperitoneal and subcutaneous, 100 ug conjugate/0.2 ml incomplete Freund's adjuvant at weeks 1, 2, 3, and 4 injected intraperitoneal and subcutaneous). Four rabbits were immunized (300 ug conjugated/1.0 ml complete Freund's adjuvant injected on day 0, 200 ug conjugate/1.0 ml incomplete Freund's adjuvant injected on days 10, 20, 30, 40 and 60).

At each time point in the mouse experiment, three mice were sacrificed, their blood collected and allowed to clot, and their antibody titers were determined by the following solid phase radio immunoassay (RIA). HTCA was coated in wells of a polyvinyl microtiter plate from solution (0.25 mg/ml). Wells were washed with phosphate buffered saline (PBS) containing TWEEN 20 and serum in 1:5 serial dilutions was added. After one hour, $^{125}$I rabbit anti-mouse immunoglobulin was added and wells were washed with PBS-TWEEN 20 to remove unbound radiolabel. Wells were punched and counted to determined titers. For the mouse study, titer is defined as the serum dilution that produces 100 counts per minute above background. Also at each time point, serum was analyzed by commercial RIA for corticosterone levels.

At each time point in the rabbit experiment, 2 ml of blood was drawn, allowed to clot, and frozen until analyses. Antibody titers were determined by an enzyme-linked immunosorbant assay (ELISA) as follows. HTCA was coated from a 0.25 mg/ml solution onto wells of a polycarbonate plate overnight. Wells were then washed and serum added in 1:5 serial dilutions. After one hour goat anti-rabbit immunoglobulin conjugated with alkaline phosphatase (1:300 dilution) was added. In one hour, wells were washed with PBS-TWEEN 20. p-nitrophenol phosphate substrate was added and allowed to react for 15 minutes before quenching with 3M NaOH. Titers were determined spectrophotometrically by absorbance at 490 nm. For the rabbit study, titer is defined as the serum dilution that produces an absorbance of 0.05 (background equals 0.01). Also at each time point, serum was analyzed by commercial RIA for corticosterone levels.

Tables 19 and 20 present and results of these experiments in terms of antibody to HTCA titers and serum corticosterone levels as a percent of controls (animals immunized with KLH alone and bled on the same schedule as those receiving HTCA).

TABLE 19

| | Mouse Experiment | |
|---|---|---|
| Day | HTCA Titer | Corticosterone (% of Control) |
| 0 | 3.6 | 100 |
| 7 | 125 | 158 |
| 14 | 3125 | 92 |
| 21 | 25300 | 78 |
| 28 | 15600 | 135 |
| 42 | 21600 | 111 |

TABLE 20

| | Rabbit Experiment | |
|---|---|---|
| Day | HTCA Titer | Corticosterone (% of Control) |
| 0 | 1.4 | 86 |
| 10 | 3.8 | 66 |
| 20 | 470 | 151 |
| 30 | 15000 | 320 |
| 40 | 104000 | 103 |

TABLE 20-continued

| | Rabbit Experiment | |
|---|---|---|
| Day | HTCA Titer | Corticosterone (% of Control) |
| 60 | 260000 | 35 |

In the mouse experiment, corticosterone levels of controls were near normal except for the last time point which was elevated to about three times normal. Corticosterone levels in control rabbits were below normal and falling between days 0 and 30 and recovered to normal levels by day 60.

In both experiments, a burst of hormone-like (ACTH) response was generated and was followed with a general depression of response. These experiments demonstrate the ability of complementary peptide antigen to moderate hormone response in vivo by stimulating antibody production with receptor binding activity. No effort was made to alter antigen presentation for the production of either agonistic or antagonistic antibodies such as might be desirable in other situations.

EXAMPLE 1R

Potential Diagnostic Assay for Adrenocorticotropic Hormone (ACTH) Based on Complementary Peptide Binding The potential for use of peptide complementary to ACTH, specifically HTCA of Example 1A, in determining ACTH levels in serum was investigated using a solid phase radiobinding assay.

Complementary peptide (HTCA) was dissolved in phosphate buffered saline (PBS) at 1 mg/ml and 200 ul aliquots were placed in wells of a 96 well polyvinyl assay plate (Microtest III, Falcon Cat. #3911). HTCA was allowed to coat the wells overnight at 4° C. The coating solution was removed and the wells were washed three times with PBS. Radiolabeled ACTH ($^{125}$I-ACTH, New England Nuclear NEX-65) was diluted into PBS containing 0.0005% TWEEN-20 so as to deliver 50 pg (or about 30,000 cpm) in a 20 ul volume.

Serum samples were prepared in a 96 well tissue culture plate by serial dilution of serum into PBS/TWEEN 20 to give a final volume of 180 ul/well. The serum samples were then transferred to the HTCA coated a ssay plate and allowed to incubate. Finally, 20 ul of $^{125}$I-ACTH solution was added, incubated, and the total sample of 200 ul was removed. After washing three times with PBS, the wells were cut from the plate and counted in a gamma counter. Nonspecific binding was determined by adding 5 ug of unlabeled ACTH to some of the samples before transferring them to the assay plate.

Serum samples used in this study contained either 50 pg/ml or 500 pg/ml of ACTH added to fetal calf serum (FCS).

The data in Table 21 shows the percent inhibition of specific $^{125}$I-ACTH binding as a function of serum dilution for both samples.

TABLE 21

| Log$_{10}$ Dilution | 50 pg/ml % Inhibition of Specific Binding | 500 pg/ml % Inhibition of Specific Binding |
|---|---|---|
| 0 | 91 | 85 |
| −0.5 | 73 | 90 |
| −1.0 | 40 | 77 |
| −1.5 | 44 | 57 |
| −2.0 | 9 | 53 |

TABLE 21-continued

| Log₁₀ Dilution | 50 pg/ml<br>% Inhibition of<br>Specific Binding | 500 pg/ml<br>% Inhibition of<br>Specific Binding |
| --- | --- | --- |
| −2.5 | 1 | 35 |
| −3.0 | 0 | 32 |
| −3.5 | 0 | 20 |

Total specific binding in this assay was determined to be 1000 counts per minute and, based on specific activity, 50% specific binding is equivalent to 0.85 pg of ACTH in a serum dilution.

For the 50 pg/ml serum sample, as determined by commercial radio-immuno assay techniques, 50% inhibition occurred at a $Log_{10}$ Dilution of −1.1 (determined by graphic interpolation). Thus, this assay measures the serum sample as 54 pg/ml, in good agreement with standard methods.

By graphic interpolation, 50% inhibition for the 500 pg/ml serum sample occurred at a $Log_{10}$ Diulution of −2.0 as expected.

These results demonstrate the feasibility of developing diagnostic assays based on complementary peptide binding.

EXAMPLE 1S

Comparison of Binding of $^{125}$I-Adrenocorticotropic Hormone to 5′-3′ and 3′-5′ Complementary Peptides A solid-phase binding assay was used to determine the ability of both the 5′-to-3′ and the 3′-to-5′-complementary-RNA-strand peptides (see Examples 1A and 1C) to bind $^{125}$I-ACTH. The peptides were diluted in phosphate-buffered saline (140 mM-NaCl/3 mM-KCl/0.1% NaN₃/20 mM-phosphate buffer, pH 7.4) to 2 mg/ml, and 0.2 ml/well was placed into poly(vinyl chloride) micro-titre plates (Becton and Dickinson, Oxnard, CA, U.S.A.). After 18 h at 4° C., unbound peptide was removed by washing three times with phosphate-buffered saline containing 0.1% bovine serum albumin (Sigma Chemical Co., St. Louis, MO, U.S.A.). $^{125}$I-ACTH was diluted to various concentrations with phosphate-buffered saline containing 0.1% bovine serum albumin and incubated in peptide-coated wells for 60 minutes at 4° C. To some wells, various concentrations of soluble peptides were added in addition to the $^{125}$I-ACTH in order to demonstrate the specificity of binding. After incubation, unbound radiolabel was washed out with phosphate-buffered saline containing 0.1% bovine serum albumin, and the radioactivity of individual wells was measured by gamma-radiation counting. The amount of specifically bound radioactivity was determined by blocking $^{125}$I-ACTH binding with unlabelled ACTH. Additional controls included coating wells with insulin or bovine serum albumin (2 mg/ml) before the addition of the $^{125}$I-ACTH.

In these experiments, half-maximal binding of $^{125}$I-ACTH occurred at 0.3 mM ACTH for both complementary peptides. Greater than 84% of binding was found to be specific and less than 5% of binding to complementary peptide plates was observed for insulin or bovine serum albumin plates. Both complementary peptides, when present in solution, competed to an equal extend to block $^{125}$I-ACTH binding to their respective sorbed counterparts.

These data demonstrate that, for the ACTH system, 5′-3′ and 3′-5′ complementary peptides are equally effective in binding ACTH.

EXAMPLE 2A

HOMOLOGIES BETWEEN PEPTIDE HORMONES AND POLY-PEPTIDES CODED BY REVERSELY-READ NUCLEIC ACIDS COMPLEMENTARY TO NUCLEIC ACIDS CODING FOR THE PEPTIDE HORMONE RECEPTOR PROTEINS.

Subtle but significant functional and structural relationships exist between peptides codingly specified by complementary strands of nucleic acids. This relationship was reflected by reading the complementary nucleic acid in the normally transcribed 5′ to 3′ direction (See, for example, Table 1, FIG. 1, and Examples 1A to 1H). When the complementary nucleic acids are read in the reverse or 3′ to 5′ direction, unique relationships of the resultant coded amino acid sequences are similarly apparent as shown in the following examples.

EXAMPLE 2B

EPIDERMAL GROWTH FACTOR (EGF), EGF RECEPTOR AND COMPLEMENTARY MESSAGE TO THE EGF RECEPTOR

The amino acid sequence of EGF and its coding nucleotide (mRNA) sequence are shown in FIG. 8 as taken from Gray et al (Nature (London, 1983), Vol. 303, p. 722) and Scott et al (Science (1983), Vol. 221, p. 236). Also shown in FIG. 8 are a partial amino acid sequence and partial coding nucleotide sequence (c-DNA) for EGF receptor as taken from Ulrich et al (Nature London, 1984), Vol. 309, p. 418).

The final column of FIG. 8 shows the nucleotide (RNA) sequence complementary to the RNA sequence which codes for the EGF receptor. An antiparallel base-pairing alignment of the EGF receptor nucleotide sequence and its complementary nucleotide sequence, was assumed. The complementary nucleotide sequence was read in the same reading frame as the coding sequence but and in the 3′ to 5′ direction. The coded amino acid sequence shown above the complementary nucleotide sequence was thus obtained. The XXX codon symbolizes termination. When the amino terminal directions of the amino acid sequences shown in FIG. 8, are in the lower numbered direction two homologous regions (appearing in boxes) of the EGF receptorcomplementary polypeptide and EGF appear. The entire EGF receptor complementary sequence (not shown) was analyzed to yield only these two complementary amino acid regions. EGF amino acid sequences 11–16 and 24–29 were found to be homologous to amino acid sequences 111–116 and 149–154 respectively coded by the nucleotide sequence complementary to that of the EGF receptor.

As shown in FIG. 8, with the two homologous regions in EGF consisting of six amino acids, five amino acids are identical in each sequence (83% homology). Furthermore, with the nucleotide sequences there is 67 and 78% nucleotide homology, respectively, between the two regions, with most of the nucleotide differences not affecting the encoded amino acids (e.g. third base changes). The two homologous amono acid regions include approximately 23% of the total EGF amino acid sequence (12 of 53 residues), and the homology is so striking that it is highly unlikely that it represents a random event. A non-random basis for this amino acid homology is strongly supported by the observation that when the sequences ASP-GLY-TYR-X-LEU-ASN and GLU-SER-LEU-X-SER-TYR (where X is any amino acid) were screened against 3060 proteins in the protein sequence bank at the National Biomedical Research Foundation (NBRF), only EGF contained these sequences. The protein sequence database at the National Biomedical Research Foundation searched was the SIAO: [Blomquist] NEW. PRO: 80 file. In total, 3,060 protein sequences were searched, which included 616,748 test segments of 6 amino acids in length or 619,803 test segments of 5 amino acids in length. So as not to bias the search for homologous sequences at positions of difference between the ligand and receptor complement sequences, any amino acid (X) was accepted as a match. Thus, the search for homologous sequences was not limited to the specific ligand or receptor complement sequences shown in FIG. 2, but rather allowed any amino acid substitution at positions of difference. Of 616,748 segments of 6 amino acids in length tested for homology, only EGF contained either of these sequences. Therefore, the relationship between these particular amino acid sequences reflects a significant relationship of EGF and its receptor.

EXAMPLE 2C

STATISTICAL SIGNIFICANCE OF AMINO ACID AND NUCLEOTIDE HOMOLOGIES BETWEEN PEPTIDE HORMONES AND POLY-PEPTIDES CODED BY NUCLEOTIDE SEQUENCES COMPLEMENTARY TO NUCLEOTIDE SEQUENCES CODING FOR PROTEINS OF THE PEPTIDE HORMONE RECEPTORS

The statistical significance of homology between any two nucleotide sequences was determined by calculating $P_a$ values, which are the probabilities that a particular homology occurred accidentally. The equation used was a summation of the Poisson distribution.

$$Pa = \sum_i^N \frac{e^{-Np}(Np)^i}{i!}$$

Where N is the length of nucleotides in the homologous sequence, i is the number of matches over the sequence and p is the probability that any given nucleotide will match. For ideal randomness, $p=0.25$ if there is no preference for any nucleotide at any position. To determine if there was any significant deviation from randomness, p values were empirically determined for all three receptors. In actuality, p values were always between 0.25 and 0.27, therefore for simplicity we assumed $p=0.25$ for calculating the Pa values. For $N=18$ and $N=15$ in sequences with ideal randomness, the number of nucleotide matches (i) equals 4.5 and 3.75, respectively. To determine the deviation from randomness of the receptor sequences for $N=18$ and $N=15$, i values were empirically determined for each receptor and found to be 4.75 (1.41) and 3.88 (1.45), respectively. To be considered statistically significant, i values had to be greater than two standard deviations from the mean (i.e. i 7.57 for $N=18$ and i 6.78 for $N=15$). Thus, Pa values $4.63 \times 10^{-2}$ for $N=18$ or $4.87 \times 10^{-2}$ for $N=15$ were considered statistically significant. Pa values that were less than or equal to $4.63 \times 10^{-2}$ for 18 nucleotides and $4.87 \times 10^{-2}$ for 15 nucleotides were determined empirically to be statistically significant. FIG. 9A shows that the nucleotide sequence homologies between EGF and the two EGF receptor complements have calculated Pa values of $1.60 \times 10^{-3}$ and $1.78 \times 10^{-4}$, respectively. Thus, the homologies between these sequences are highly significant with the number of base matches being greater than five standard deviations from the means for ideal randomness.

In further analyses, performed generally according to the procedure of Example 2B, the relationships of other peptide hormones and their receptors and receptor complementary polypeptides were elucidated.

The amino acid and nucleotide sequences shown in FIG. 9B were obtained from the following sources:

Interleukin -2 (IL-2) from Taniguchi et al (Nature (Landon, 1984) Vol. 302, p. 305) and Devos et al (Nucl. Acid Res. (1983) Vol. VII, p. 4307).

Interleukin -2 Receptor (IL-2 Receptor) from Nikaido et al (Nature (London, 1984) Vol. 311, p. 631).

Transferrin (TF) from Yang et al (Proc. Nat'l. Acad. Sci. (1984) Vol. 81, p. 2752.

Transferrin Receptor (TF Receptor) from Schneider et al (Nature (London, 1984) Vol. 311, p. 675).

As shown in FIGS. 9A and 9B, results similar to those found with the EGF system were found when IL-2 and TF were searched for homology with their corresponding receptor complements. For IL-2, two homologous regions of 6 and 5 amino acids were found (FIG. 9A) with 83 and 80% amino acid homology, respectively. In addition, the nucleotide homology between the two sequences (61 and 67%, respectively) was highly significant ($Pa=4.26 \times 10^{-3}$ and $3.56 \times 10^{-3}$, respectively). Both amino acid sequences (LEU-GLU-X-LEU-LEU-LEU and TYR-ARG-MET-X-LEU, where X is any amino acid) were screened for homologies with 3060 proteins in the NBRF sequence bank.

For 616,748 test segments of six amino acids in length, only 7 proteins, including IL-2, were found to have homology with LEU-GLU-X-LEU-LEU-LEU. When the sequence LEU-GLU-X-LEU-LEU-LEU (where X is any amino acid) was screened for homologies against 616,748 test segments of 6 amino acids in length, seven proteins contained homologous sequences. These included human IL-2, human and mouse Ig alpha heavy chain, arabinose operon regulatory protein from *E. coli* and *S. typhimurium*, gene k protein of OX-174 and protein 4 from *Aspergillus amstelodami* mitochondria. However, only one protein (IL-2) contained complete homology with IL-2 where X==HIS and only one protein (Protein 4 from Aspergillus amstelodami mitochondria) contained complete homology with the IL-2 receptor complement where X=THR. When the sequence TYR-ARG-MET-X-LEU was screened against 619,803 segments of five amino acids in length, only IL-2 and the hemoglobin alpha chain of the South African toad contained homologous sequences. Taken together, the two homologous sequences were found to be uniquely associated with IL-2.

For TF and its receptor complement, there were many regions of significant sequence homology, however it should be noted that, due to space limitations, not all regions of homology are shown. The representative sequences shown in FIG. 9B have at least 53% nucleotide homology and have Pa values below those considered statistically significant. When the amino acid sequences ILE-PRO-X-GLY-LEU-LEU and GLU-PHE-X-LEU-PHE-SER (where X is any amino acid) were screened for homologies against 3,060 proteins in the NBRF sequence bank, only TF contained both sequences. The latter sequence was only found in transferrin while ILE-PRO-X-GLY-LEU-LEU was found in transferrin, lactotransferrin and only three unrelated proteins (bacterial tryptophan synthase, *E. coli* colicin E1 immunity protein and influenza C hemagglutinin precursor).

EXAMPLE 2D

From the results presented in Example 2C there can be little doubt that the nucleotide sequences for ligands and receptors contain highly significant regions of complementarity. At the present time these were the only ligand-receptor pairs for which the complete amino acid and nucleotide sequences were known. Thus, all the sequence data available to date supports the hypothesis that receptor and ligand binding sites could have evolved from complementary strands of nucleic acid. There are several observations supporting the idea that the complementary regions shown here may in fact code for amino acid sequences in the binding site of the receptor. First, the complementary nucleotide sequences were always detected in the portion of the receptor external to the cytoplasmic membrane. For example, the two homologous sequences detected in the EGF receptor complement were in the 100,000 dalton external domain (the domain which binds EGF in the receptor) whereas no homologies were detected in the 60,000 dalton cytoplasmic domain (the domain with protein kinase activity). This finding was also true for the IL-2 and TF receptors sequences, since in all instances homologies were in the external portion which contributes to ligand binding. Secondly, for the ligand, their size (5-6 amino acids) approximates what one might expect to fill a complete receptor site if one used antibody combining sites for an example as shown in Nisonoff et al (The Antibody Molecule (Academic Press. N.Y. 1984) pp. 29-38). These sequences appear to represent binding sites, one of which would be expected to be at each point of contact between the receptor and ligand. Third, and most importantly, it has been demonstrated, as earlier described herein, that the hormones ACTH and gamma-endorphin bind with high affinity to synthetically derived peptides encoded by RNA complementary to the respective hormone mRNA. This observation demonstrates that amino acid sequences complementary to a peptide do in fact bind that peptide, and therefore the sequence complementary to the peptide must contain a receptor-like binding site. Furthermore, the "synthetic" binding site for ACTH was antigenically related to an ACTH adrenal cell receptor. In total, these observations indicate that peptide-receptor binding sites may ultimately be derived from complementary strands of nucleic acid.

If protein-protein binding interactions evolving from complementary strands of nucleic acids prove to be as general a phenomenon in biology as discerned, there are many potential applications for this concept. For example, the knowledge of ligand sequences would allow easy purification and characterization of receptors using methodology similar to that previously described herein. Valuable information concerning ligand conformations in binding site environments may be obtained by constructing well defined ligand-"binding site" pairs. Ultimately, knowledge of the binding site sequences for receptor-ligand pairs will allow construction of small, well defined receptor agonists, and/or antagonists valuable for manipulating biological responses. These findings may also be important in the investigation and understanding of differentiation and embryogenesis. For instance, the mere transcription of a DNA sequence by one cell and its complement by another could allow for cellular recognition and communication via the resulting peptides or proteins which interact. The concepts described herein may, for instance, provide a genetic and molecular basis for internal imaging in the immune system and circuit formation in the central nervous system.

The discoveries described herein, particularly in Examples 2A to 2C, describe a process for preparing polypeptides having an affinity for cellular receptor sites of particular peptide hormones. Said process comprises a series of steps. First, a second nucleotide sequence of a second nucleotide strand base-pairing with a first nucleotide strand coding for at least a portion of a proteinoceous component of a peptide hormone receptor site is ascertained. Homologous amino acid sequences between the peptide hormone and the amino acid sequence coded by the second nucleotide sequence, when read in the 3' to 5' direction, are then determined.

Having found these homologous amino acid sequences, which appear responsible for the characteristic binding of peptide hormones to their receptor sites, polypeptides comprising at least a portion of at least one of said homologous sequences may be prepared for example, by routine chemical or biological synthetic methods. These polypeptides, containing key regions of homology and receptor binding affinity with a peptide hormone or ligand, may be screened by commonly utilized techniques as agonists or antagonists for the peptide hormone or ligand.

EXAMPLE 3A

Angiotensin II and the Design and Obtaining of Complementary Peptides Based on Nucleic Acid Sequences The Angiotensin system is shown below:

Angiotensinogen $\xrightarrow{1}$ Angiotensin I $\xrightarrow{2}$ Angiotensin II Reaction 1 is an enzymatic cleavage by the enzyme renin and reaction 2 is an enzymatic cleavage by angiotensin converting enzyme (ACE). Angiotensinogen contains 453 amino acid residues, Angiotensin I consists of the 10 N-terminal residues of Angiotensinogen, and Angiotensin II contains the 8 N-terminal residues of Angiotensin I. Angiotensin II is the active molecule that controls blood pressure regulation.

The nucleic acid sequence for rat Angiotensin II was obtained from Ohkubo et al. (Proc. Nat. Acad. Sci. U.S.A., 80, p. 2197-2200, 1983) by translating the entire mRNA for angiotensinogen and observing the amino acid sequence (from base 134 through 157) known to the Angiotensin II. The sequence, its translation, its complement, and the complementary amino acids determined by 3' and 5' reaading are shown in the following table:

| Angiotensin II | ASP | ARG | VAL | TYR | ILE | HIS | PRO | PHE | Carboxy Terminus |
|---|---|---|---|---|---|---|---|---|---|
| mRNA | GAC | CGC | GUA | UAC | AUC | CAC | CCC | UUU | 3' Terminus |
| cRNA | CUG | GCG | CAU | AUG | UAG | GUG | GGG | AAA | 5' Terminus |

| | | | | | | | |
|---|---|---|---|---|---|---|---|
| -continued | | | | | | | |
| 3' Reading | LEU | ALA | HIS | MET | END | VAL | GLY | LYS |
| 5' Reading | VAL | ALA | TYR | VAL | ASP | VAL | GLY | LYS |

Since 3' reading gave a termination signal (UAG-/END), ASP was substituted for END. Complementary peptides were obtained by conventional solid-phase synthesis from Triton Biosciences Inc. (Alameda, Calif.) for the following complementary peptides. Note that two peptides have parallel peptide bond orientations and two have antiparallel.

| Designation | SEQUENCE | | | | | | | |
|---|---|---|---|---|---|---|---|---|
| | N Terminus | | | | C Terminus | | | |
| 5CA-AII Rat | LYS | GLY | VAL | ASP | VAL | TYR | ALA | VAL |
| 3CA-AII Rat (4ASP) | LYS | GLY | VAL | ASP | MET | HIS | ALA | LEU |
| 5CP-AII Rat | VAL | ALA | TYR | VAL | ASP | VAL | GLY | LYS |
| 3CP-AII Rat (5ASP) | LEU | ALA | HIS | MET | ASP | VAL | GLY | LYS |

EXAMPLE 3B

Angiotensin II and the Design and Obtaining of Complementary Peptides Based on Amino Acid Sequences (Consensus Complements)

The amino acid sequence of human Angiotensin II was taken from the sequence of a fragment of human Angiotensinogen determined by Tewksbury et al. (BBRC, 99, p. 1311-1315, 1981).

Using the substitutions given in Table 6A two consensus complements of Angiotensin II were designed, one with parallel peptide bond orientation and one with anti-parallel orientation as shown below:

CCA-AII LYS—GLY—VAL—TYR—ILE—HIS—ALA—LEU
CCP-AII LEU—ALA—HIS—ILE—TYR—VAL—GLY—LYS

These complementary peptides were obtained by conventional solid-phase synthesis from Triton Biosciences Inc. (Alameda, Calif.).

EXAMPLE 3C

Angiotensin II and Design and Obtaining of Complementary Peptides Based on Amino Acid Sequences (Simplified Complements)

Using the amino acid sequence for Angiotensin II from the prior example and the substitutions given in Table 6C, the following (anti-parallel) simplified complementary peptide to Angiotensin II (human) was designed.

SCA-AII
GLU-GLY-LEU-GLU-LEU-GLU-ALA-LEU

This complementary peptide was obtained by conventional solid-phase synthesis from Triton Biosciences Inc. (Alameda, Calif.).

EXAMPLE 3D

Angiotensin and Design and Obtaining of Related Complementary Peptides

Based on the known network of reactions in the angiotensin system, complementary peptides were prepared that could reveal multiple beneficial effects.

Molecules are designed, based on the complementary peptide binding observations, that can specifically interact with one or more of the angiotensin system molecules. As a result of such interactions, an angiotensin molecule will not undergo enzymatic reaction. Thus, the conversion of, for example, angiotensin I to Angiotensin II could be reduced without actually inhibiting ACE or its other functions.

Based on the human angiotensinogen fragment sequence for Example 3B, the following two peptides were designed using the consensus complenment method.

CCA-AI          GLU—VAL—LYS—GLY—VAL—TYR—ILE—HIS—ALA—LEU
CCA-A(1-13) VAL—TYR—HIS—GLU—VAL—LYS—GLY—VAL—TYR—ILE—HIS—ALA—LEU

These complementary peptides were obtained by solid-phase synthesis from Triton Biosciences Inc. (Alameda, Calif.).

The molecule CCA-A(1-13) might be expected to bind all three members of the angiotensin family shown above, and thereby inhibit reactions 1 and 2 and inhibit the ability of Angiotensin II to activate its receptor.

EXAMPLE 3E

Angiotensin II and the Design and Obtaining of Potentially Metabolically Stable Complementary Peptides Based on the structure of one of the complementary peptides of angiotensin II (CCA-AII, Example 3B) several derivatives were designed that might show improved metabolic stability to various peptidases. Both amino-and carboxy- peptidases are known to be present in many organisms. It is known that many modifications to peptide structures can protect peptides from the action of these enzymes. Acylation (Ac) of terminal amino groups and prolyation and amidation (Am) of terminal carboxy groups are common methods to protect peptides from amino- and carboxy- peptidases, respectively.

The following molecules were designed based on these principles and the structure of the active complementary peptide CCA-AII.

| Designation | Structure |
|---|---|
| CCA-AII (Am) | LYS—GLY—VAL—TYR—ILE—HIS—ALA—LEU—Am |
| CCA-AII (PR09) | LYS—GLY—VAL—TYR—ILE—HIS—ALA—LEU—PRO |
| CCA-AII (Ac, Am) | Ac—LYS—GLY—VAL—TYR—ILE—HIS—ALA—LEU—Am |

| Designation | Structure |
|---|---|
| CCA-AII (Ac, PR09) | Ac—LYS—GLY—VAL—TYR—ILE—HIS—ALA—LEU—PRO |

The molecules were obtained by conventional solid-phase chemistry from Triton Biosciences Inc. (Alameda, Calif.). Amide resins were used in solid-phase synthesis to obtain admidated peptides. Acylation was carried out by reacting acetic anhydride with fully protected peptide while still on the resin of the solid-phase synthesis.

Another method to protect peptides from enzymatic attack is to substitute D-amino acids for the naturally occuring L-amino acids. For this reason, an all D complementary peptide was designed based on the sequence of CCA-AII (Example 3B).

CCA-AII (all D)
LYS-GLY-VAL-TYR-ILE-HIS-ALA-LEU

This molecule was obtained by conventional solid-phase synthesis from Triton Biosciences Inc. (Alameda, Calif.).

EXAMPLE 3F

Effect of Peptides Complementary to Angiotensin II on the Binding of Radiolabelled Angiotensin II to its Receptor Inhibition of angiotensin II binding to angiotensin II receptors by complementary peptides was tested with measurement through the use of radioactive angiotensin II. Rabbit livers were homogenized, and were centifuged in order to isolate particles sedimenting between 1,000 and 100,000 xg. Binding activity was solublized with 1% digitonin, followed by ammonium sulfate fractionation between 49 and 65% satuation followed by DEAE- cellulose chromatography at pH 7.5 using a linear gradient between 0.0 and 0.3M KCl. The partially purified, solubilized receptor preparation bound 17 pmoles of angiotensin II per ng protein when analyzed by Scatchard analysis, indicating a purity of approximately 0.1%.

The standard assay for binding of angiotensin II to the receptor is as follows: The complete system (150 µl) contains 30 mM Tris-HCl, pH 7.5, 2.5 mM K$_2$EDTA, 0.2 mM PCMS, 0.25 nM [$^{125}$I] angiotensin II (ca. 100,000 cpm), 100 µg BSA, 0.25% (V/V) Brij 99 and 30 µg of partially purified receptor. The reaction is initiated by addition of the receptor and samples are incubated for 60 minutes at 20° C. The reaction is terminated with 1 ml of cold 0.5% charcoal/0.05% Dextran in 100 mM Tris-HCl, pH 7.5. Tubes are vortexed and then allowed to stand 10 minutes at 4° C., after which they are centrifuged and their supernatants, containing protein-bound angiotensin II, are counted.

The complete system under these conditions regularly yields about 10,000 cpm of bound radioactivity. A control lacking receptor yields values of 50-200 cpm which were subtracted from these data. Values of 50-2000 cpm were obtained when 120 µM cold antiotensin II is present in the reaction mixture indicating that virtually all binding is specific. A sample including 20 nM cold angiotensin II was also run. Residual binding of radioactivity in this control was 35-45%. Complementary peptides to angiotensin II were dissolved in water, except for CCA-A (1-13) which was dissolved in 3% DMSO, 0.04M acetic acid and 0.05M HCl. Results of these assays are given in Table 22. ID$_{50}$ is the concentration of peptide that inhibits binding of radiolabelled angiotensin II by 50%.

TABLE 22

Inhibition by Complementary Peptides of Angiotensin II Binding to Isolated Hepatic Receptor

| Peptide | ID$_{50}$ (nM) |
|---|---|
| Angiotensin II | 15 |
| CCA-AII | 8-14 |
| CCA-A (1-13) | 40 |
| CCA-AI | 490 |
| CCA-AII (Am) | 160 |
| CCA-AII (Ac, Am) | 3,100 |
| CCA-AII (Pro 9) | 40 |
| CCA-AII (Ac, Pro 9) | 1,350 |
| CCA-AII (all D) | >10,000 |
| 5CA-AII Rat | 4,000 |
| 3CA-AII Rat (4 ASP) | 5,000 |
| 5CP-AII Rat | >10,000 |
| 3CP-AII Rat (5 ASP) | >10,000 |

EXAMPLE 4A

Luteininzing Hormone Releasing Hormone (LHRH) and the Design and Obtaining of a Complementary Peptide Luteinizing hormone releasing hormone has a wide variety of biological effects and receptors for it occurs presumably on many cell types (Miller, et al. Nature, 313, p. 231-233, 1985). The nucleic acid sequence for the precursor form of LHRH has been reported (Seeburg and Adelman, Nature, 311, p 666-668, 1984) and was used in the following design of a complementary peptide. The sequence for LHRH, its translation, its complement, and the 5'-3' translation of its complement are shown below.

| LHRH | GLN—HIS—TRP—SER—TYR—GLY—LEU—ARG—PRO—GLY | C terminus |
|---|---|---|
| mRNA | CAG—CAC—TGG—TCC—TAT—GGA—CTG—CGC—CCT—GGA | 3' terminus |
| cRNA | GTC—GTG—ACC—AGG—ATA—CCT—GAC—GCG—GGA—CCT | 5' terminus |
| 5CA—LHRH | LEU—VAL—PRO—GLY—ILE—SER—GLN—ALA—ARG—SER | N terminus |

The complementary peptide 5CA-LHRH was obtained by solid-phase synthesis from Triton Biosciences Inc. (Alameda, Calif.).

EXAMPLE 4B

Effect of a Peptide Complementary to LHRH (5CA-LHRH) on LHRH-Stimulated LH Release from Pituitary Cells A reverse hemolytic plaque assay (Smith, et al.), Method in Enzymology, 124, p. 443) was used to examine the effect of a peptide (5CA-LHRH) complementary to LHRH on LHRH-stimulated release of LH from pituitary cells. The assay was performed as referenced, except that in the experiments labelled as (Pre), the complementary peptide and LHRH were preincubated for 1 hour before addition to dispersed pituitary cells.

Plaques were analyzed by determining plaque area with an image analysis (Bioquant or Image Technology Corp. Model 300) of 125×-500× microscopic enlargements. Results are presented as the percentage response of a particular assay to control assay (plaques formed under stimulation by $5 \times 10^{-10}$M LHRH).

The effect of the complementary peptide (5CA-LHRH) is presented in Table 23:

TABLE 23

| Treatment | Exp. 1 (Pre) | Exp. 2 (No) | Exp. 3 (Pre) | Exp. 4 (Pre) | Exp. 5 (No) |
|---|---|---|---|---|---|
| None | 7 | 5 | 0.03 | 2 | 2 |
| Control $5 \times 10^{-10}$ M LHRH | 100 | 100 | 100 | 100 | 100 |
| $5 \times 10^{-10}$ M LHRH + 5CA—LHRH | | | | | |
| $10^{-4}$ M | 77 | 61 | NT | 52 | 52 |
| $10^{-5}$ M | 82 | 52 | 68 | 63 | 70 |
| $10^{-6}$ M | 110 | 74 | 98 | 81 | 81 |
| $10^{-7}$ M | 101 | 74 | 88 | 78 | 115 |
| $10^{-8}$ M | 105 | 83 | NT | 96 | 92 |
| $10^{-9}$ M | 119 | 84 | NT | 95 | 123 |
| $5 \times 10^{-10}$ M | 103 | NT | NT | NT | NT |
| LHRH + Somatostatin $10^{-4}$ M 5CA—LHRH | | | | | |
| $10^{-5}$ M | NT | NT | 2.7 | NT | NT |
| $10^{-6}$ M | NT | NT | 0.5 | NT | NT |
| $10^{-7}$ M | NT | NT | 0.5 | NT | NT |

The results show a clear inhibition of the effects of LHRH in this assay by the complementary peptide 5CA-LHRH.

EXAMPLE 4C

EFFECT OF ANTIBODY TO 5CA-LHRH (A5CALHRH) ON LHRH-STIMULATED LH SECRETION BY PITUITARY CELLS

The reverse hemolytic plaque assay for LH secretion by dispersed pituitary cells of proestrous rats were performed essentially as described in Example 4B, except that the pituitary cells were preincubated with A5-CALHRH or the normal rabbit serum (NRS) for two hours. After washing, reverse hemolytic plaque formations was initiated with the addition of LHRH and anti-LH antiserum. Two hours later, complement was added for 30 minutes. A5CALHRH at the same concentration was also added during reverse hemolytic plaque formation. A5CALHRHB1 is the IgG fraction of antiserum from the first bleed at 40 days after immunization of a male rabbit with 5CA-LHRH coupled to Keyhole Limpet Hemocyanin (300 ug antigen in 1 ml complete Freund's adjuvant, initial injection Day O, 200 ug antigen in 1 ml incomplete Freund's adjuvant, injections on days 10, 20, 30, 40, 50 and 60). A5CALHRHB3 is from the third bleed of the rabbit at day 60. F(ab)2 fragments of A5CALHRHB1 were produced by conventional methods (*Methods In Immunology*, 3rd ed., p. 256, 1977). Results are shown in Table 24.

TABLE 24

| Treatment | % Control |
|---|---|
| None | 20 |
| LHRH $5 \times 10^{-10}$M | 100 (Control) |
| A5CALHRHB1 | |
| 1:10 + LHRH $5 \times 10^{-10}$M | 140 |

TABLE 24-continued

| Treatment | % Control |
|---|---|
| 1:25 + LHRH $5 \times 10^{-10}$M | 158 |
| 1:100 + LHRH $5 \times 10^{-10}$M | 178 |
| A5CALHRHB1 F9Ab)₂* | |
| 1:10 + LHRH $5 \times 10^{-10}$M | 75 |
| 1:25 + LHRH $5 \times 10^{-10}$M | 132 |
| 1:100 + LHRH $5 \times 10^{-10}$M | 146 |
| NRS | |
| 1:10 + LHRH $5 \times 10^{-10}$M | 78 |
| 1:25 + LHRH $5 \times 10^{-10}$M | 118 |
| 1:100 + LHRH $5 \times 10^{-10}$M | 93 |
| A5CALHRHB3 | |
| 1:5 | 5 |
| 1:10 | 3 |
| 1:25 | 10 |
| 1:100 | 28 |
| A5CALHRHB3 | |
| 1:5 + LHRH $5 \times 10^{-10}$M | 27 |
| 1:10 + LHRH $5 \times 10^{-10}$M | 25 |
| 1:25 + LHRH $5 \times 10^{-10}$M | 46 |
| 1:100 + LHRH $5 \times 10^{-10}$M | 184 |

*Pituitary cells are reported to have receptors for the FC portion of antibody molecules. (Pouglane et al, Nature 261, 142 (1976), Buffa et al Histochem 63 15 (1979)) F(Ab)₂ fragments of A5CALHRH were prepared to ensure that any effect on LHRH stimulation of pituitary to interaction of A5CALHRH with nonspecific FC receptors.

These results show the presence of both antagonistic and agonistic antibodies in the immune serum of rabbits immunized with a peptide complementary to LHRH.

EXAMPLE 4D

Immunocytochemical Assay for LHRH Cell Surface Receptors Based on Antibodies to Peptides Complementary to LHRH Various cells have receptors for LHRH on their surfaces. It is well-known that 5% of pituitary cells have such receptors since they respond to LHRH by releasing LH. The following experiments were performed to demonstrate the ability of antibodies to peptides complementary to LHRH to specifically label those pituitary cells containing LHRH receptors.

After standard plaque assays were performed (as in Example 4B), the chambers were infused with sodium acetate to elute the bound antibodies and fixed sequentially in B5 fixative, ethanol, Lugol's iodide and sodium thiosulfate (as described in Smith et al., *Methods in Enzymology*, 124, p. 443). The slides were treated with hydrogen peroxide and normal goat serum before application of suitable dilutions of the antibodies. Immunocytochemistry was performed with the ABC method (Vector Labs, Burlingame, Calif.) with diaminobenzidine as substrate.

Cells containing LH were selectively stained with antibodies to LH. In general, plaques formed in the assays of earlier examples contained one LH-containing cell near the center of each circular plaque. Cells presenting LHRH receptors were stained using IgG fractions of immune serum from rabbits immunized with a peptide complementary to LHRH (see Example 4C). Again, one cell per circular plaque was stained and these were the same cells that contained LH. Control experiments demonstrated that receptor staining by antibody to the complement of LHRH could be blocked with both LHRH (by binding to receptor) and by the complement to LHRH (by binding to the antibody).

These experiments demonstrate that the antibodies to the complement of LHRH selectively stain pituitary cells that present LHRH receptors.

EXAMPLE 5A

Ribonuclease A S-Peptide and the Design and Obtaining of a Complementary Peptide Treatment of bovine ribonuclease A (RNase), a 124 amino acid protein, with the proteolytic enzyme, subtilisin, cleaves RNase into two fragments designated S-peptide, amino acid residues 1-20, and S-protein, amino acid residues 21-124. The m-RNA sequence for rat RNase was obtained from MacDonald et al. (J. Biol. Chem., 257, p. 14,582-14,585, 1982), which shows substantial sequence homology with bovine RNase. Residues 4 through 23 share homology with the S-peptide of bovine S-peptide. A putative M-RNA structure for bovine RNase was derived by making the minimal number of base changes in the rat m-RNA sequence and is shown in the following table:

Rat RNase amino acid residues 4-23 ARG GLU SER SER ALA ASP LYS PHE LYS ARG GLN HIS MET ASP THR GLU GLY PRO SER LYS.

Rat m-RNA sequence for rat RNase residues 4-23 reading 5' to 3' AGG GAA UCA UCG GCG GAU AAG UUU AAG AGG CAG CAC AUG GAC ACA GAG GGU CCC UCC AGG Putative m-RNA for bovine S-peptide reading 5' to 3' AAG GAA ACA GCG GCG GCU AAG UUU GAG AGG GAG CAC AUG GAC UCA UCG ACU UCC GCC GCG Amino acid sequence of bovine S-peptide LYS GLU THR ALA ALA ALA LYS PHE GLU ARG GLU HIS MET ASP SER SER THR SER ALA ALA The amino acids for the complementary peptide to bovine S-peptide were determined from the nucleic acid structure by reading the complementary strand in the 5' to 3' reading frame as shown in the following table:

Complementary nucleic acid structure for bovine S-peptide CGC GGC GGA AGU CGA UGA GUC CAU GUG CUC CCU CUC AAA CUU AGC CGC CGC UGU UUC CUU The parallel complementary amino acid sequence for bovine S-peptide LEU PHE SER ARG ARG SER LEU LYS LEU PRO LEU VAL HIS VAL SER ARG SER GLY GLY ARG Since the sixth codon gave a termination signal (UGA/END), SER was substituted for END. For codon 18 (UGU/CYS), SER was substituted for CYS. These amino acid substitutions maintain second base complementarity with the bovine S-peptide. The complementary peptide was obtained by conventional solid-phase synthesis from Triton Biosciences Inc. (Alameda, Calif.).

EXAMPLE 5B

Ribonuclease A S-Peptide and the Binding and Purification of a Complementary Peptide The interaction of the S-peptide complementary peptide with S-peptide was examined by covalently coupling S-peptide to a N-hydroxysuccinimide activated silica gel bonded phase using conventional chemistry. The peptide mixture obtained from hydrogen fluoride treatment of the complementary peptide using conventional chemistry was applied directly to the S-peptide chromatographic column (3 mm by 44 mm), previously equilibrated at either 0.10M Tris-acetate, pH 7.0, or 0.10M Tris-acetate, pH 5.1, at a flow rate of 1 ml/min. The column effluent was monitored by absorbance at 226 nm. Under these conditions, a large peak composed of peptide and non-peptide material was obtained at the solvent front. The column was washed with 45 ml of buffer, followed by 30 ml of water, and then 0.10M acetic acid was applied to the column which eluted 226 nm absorbing material. Chromatography of this eluted material on a Waters reversed phase C-18 column using a flow rate of 1 ml/min and a gradient elution for 10% solution A to 40% solution B over 35 min (solution A, 0.1% trifluoroacetic acid/water; solution B, 0.1% trifluoroacetic acid/100% acetonitrile) gave a single peak with a retention time of approximately 26 minutes. Sequencing this material using a gas phase sequenator (Applied Biosystems, Foster City, Calif.) confirmed that its structure was identical to the synthesized complementary peptide. Control peptides did not bind to the S-peptide affinity column. These results demonstrate a specific binding between the S-peptide and one of its complements and also demonstrates that the S-peptide affinity column can be used to purify crude preparations of peptide.

Changes may be made in the construction, operation and arrangement of the various amino acids, elements, steps and procedures described herein without departing from the concept and scope of the invention as defined in the following claims.

What is claimed is:

1. A method for determining the amino acid sequence of a polypeptide having a minimum complementary peptide binding activity for at least a portion of an original peptide or protein comprising the steps of:
   (a) determining a first nucleotide sequence of a first nucleic acid, said first nucleotide sequence coding for an amino acid sequence of at least a portion of an original peptide or protein;
   (b) ascertaining a second nucleotide sequence of a second nucleic acid which base-pairs with the first nucleotide sequence of the first nucleic acid, the first and second nucleic acids pairing in antiparallel directions;
   (c) determining the amino acid sequence of the complementary polypeptide by finding the amino acid sequence coded by the second nucleotide sequence when read in the same reading frame as the first nucleotide sequence.

2. The method of claim 1 wherein the second nucleotide sequence is read in the 5' to 3' direction.

3. The method of claim 1 wherein the second nucleotide sequence is read in the 3' to 5' direction.

4. The method of claim 1 wherein the first nucleic acid is defined further as being DNA.

5. The method of claim 1 wherein the first nucleic acid is defined further as being messenger RNA.

6. A method for obtaining a polypeptide having a minimum complementary peptide binding activity for at least a portion of an original peptide or protein comprising the steps of:
   (a) determining a first nucleotide sequence of a first nucleic acid, said first nucleotide sequence coding for an amino acid sequence of at least a portion of an original peptide or protein;
   (b) ascertaining a second nucleotide sequence of a second nucleic acid which base-pairs with the first nucleotide sequence of the first nucleic acid, the first and second nucleic acids pairing in antiparallel directions;

(c) determining the amino acid sequence of the complementary polypeptide by finding the amino acid sequence coded by the second nucleotide sequence when read in the same reading frame as the first nucleotide sequence; and (d) obtaining a polypeptide comprising the amino acid sequence determined in step c.

7. The method of claim 6 wherein step (d) is defined further as comprising chemically synthesizing said polypeptide.

8. The method of claim 6 wherein step (d) is defined further as obtaining said polypeptide from a protein or larger polypeptide including said amino acid sequence.

9. The method of claim 6 wherein the second nucleic acid is defined further as being DNA and step (d) is defined further as comprising insertion of the second nucleotide sequence into a plasmid to form a recombinant DNA vector and transforming a unicellular organism therewith to produce a transformant unicellular organism biosynthesizing said complementary polypeptide.

10. The method of claim 1 wherein the first nucleic acid is defined further as being DNA.

11. The method of claim 9 wherein the unicellular organism is selected from the group consisting of bacteria, and yeast.

12. The method of claim 6 wherein the second nucleotide sequence is read in the 5' to 3' direction.

13. The method of claim 6 wherein the second nucleotide sequence is read in the 3' to 5' direction.

14. The method of claim 6 wherein the first nucleic acid is defined further as being DNA.

15. The method of claim 8 wherein the first nucleic acid is defined further as being messenger RNA.

16. A method for preparing a polypeptide having a minimum complementary peptide binding activity for the cellular receptor site for a particular peptide ligand, comprising the steps of:

ascertaining a second nucleotide sequence of a second nucleotide strand base-pairing with a first nucleotide strand coding for at least a part of a protein portion of a peptide ligand receptor site;

determining any amino acid sequences in the peptide ligand which are homologous to amino acid sequences coded by the second nucleotide sequence when said second sequence is read in a 3' to 5' direction; and preparing a polypeptide comprising at least a portion of at least one of said homologous amino acid sequences.

17. A method for preparing polypeptides having a minimum complementary peptide binding activity for a polypeptide ligand based on its cellular receptor site comprising the steps of:

ascertaining a second nucleotide sequence of a second nucleotide strand base-pairing with a first nucleotide strand coding for at least a part of a protein portion of a peptide ligand receptor site;

determining any amino acid sequences in the peptide ligand that are homologous to amino acid sequences coded by the second nucleotide sequence when said second sequence is read in a 3' to 5' or 5' to 3' direction;

determining the amino acid sequences of the receptor site for the polypeptide ligand that correspond to the homologous amino acid sequences of the preceding step; and preparing a polypeptide comprising at least a portion of at least one of said amino acid sequences of the receptor site.

* * * * *

UNITED STATES PATENT AND TRADEMARK OFFICE
CERTIFICATE OF CORRECTION

PATENT NO. : 5,077,195

DATED : December 31, 1991

INVENTOR(S) : J. Edwin Blalock et al.

It is certified that error appears in the above-identified patent and that said Letters Patent is hereby corrected as shown below:

In claim 15, column 51, line 33, delete the numeral "8" and insert the numeral -6- therefor.

Signed and Sealed this

Twentieth Day of April, 1993

Attest:

MICHAEL K. KIRK

*Attesting Officer*    Acting Commissioner of Patents and Trademarks